United States Patent
Imade

(10) Patent No.: US 10,542,875 B2
(45) Date of Patent: Jan. 28, 2020

(54) IMAGING DEVICE, ENDOSCOPE APPARATUS, AND IMAGING METHOD

(71) Applicant: OLYMPUS CORPORATION, Tokyo (JP)

(72) Inventor: Shinichi Imade, Iruma (JP)

(73) Assignee: OLYMPUS CORPORATION, Tokyo (JP)

(*) Notice: Subject to any disclaimer, the term of this patent is extended or adjusted under 35 U.S.C. 154(b) by 84 days.

(21) Appl. No.: 15/982,313

(22) Filed: May 17, 2018

(65) Prior Publication Data
US 2018/0263474 A1    Sep. 20, 2018

Related U.S. Application Data

(63) Continuation of application No. PCT/JP2015/083774, filed on Dec. 1, 2015.

(51) Int. Cl.
  *A62B 1/04* (2006.01)
  *A61B 1/00* (2006.01)
  (Continued)

(52) U.S. Cl.
  CPC ...... *A61B 1/00193* (2013.01); *A61B 1/00009* (2013.01); *A61B 1/045* (2013.01); *G02B 23/2415* (2013.01); *A61B 1/00188* (2013.01); *A61B 1/042* (2013.01); *A61B 1/05* (2013.01); *A61B 1/06* (2013.01)

(58) Field of Classification Search
  CPC .. H04N 5/238; H04N 5/23212; H04N 13/218; H04N 13/211; G03B 7/08; G03B 11/00; G02B 27/0988; G02B 23/2415; G02B 23/2484; A61B 1/00193; A61B 1/00009; A61B 1/0005; A61B 1/00186;
  (Continued)

(56) References Cited

U.S. PATENT DOCUMENTS

2010/0208046 A1   8/2010   Takahashi
2016/0028940 A1*  1/2016   Izawa ............... G03B 17/20
                                           348/349

FOREIGN PATENT DOCUMENTS

JP    2000-102040 A    4/2000
JP    2010-128354 A    6/2010
JP    2014-028008 A    2/2014

OTHER PUBLICATIONS

International Search Report dated Mar. 1, 2016 issued in PCT/JP2015/083774.

* cited by examiner

*Primary Examiner* — Sath V Perungavoor
*Assistant Examiner* — Peet Dhillon
(74) *Attorney, Agent, or Firm* — Scully, Scott Murphy & Presser, P.C.

(57) ABSTRACT

An imaging device includes an image sensor, an optical system forming an image of an object on the image sensor, and a processor. The optical system switches between a first state of capturing an image of the object with a single pupil and a second state of capturing an image of the object with two pupils. The processor generates a simulative phase difference image from a first captured image captured with the image sensor in the first state, and executes matching processing of comparing the simulative phase difference image with a second capture image captured with the image sensor in the second state to detect a phase difference between an image formed with one of the two pupils and an image formed with another one of the two pupils.

15 Claims, 17 Drawing Sheets

(51) Int. Cl.
  *A61B 1/045* (2006.01)
  *G02B 23/24* (2006.01)
  *A61B 1/04* (2006.01)
  *A61B 1/05* (2006.01)
  *A61B 1/06* (2006.01)

(58) Field of Classification Search
  CPC ..... A61B 1/045; A61B 1/00188; A61B 1/042; A61B 1/05; A61B 1/06
  See application file for complete search history.

IMAGING DEVICE, ENDOSCOPE APPARATUS, AND IMAGING METHOD

CROSS REFERENCE TO RELATED APPLICATION

This application is a continuation of International Patent Application No. PCT/JP2015/083774, having an international filing date of Dec. 1, 2015, which designated the United States, the entirety of which is incorporated herein by reference.

BACKGROUND

The present invention relates to an imaging device, an endoscope apparatus, an imaging method, and the like.

Techniques for optically measuring a three-dimensional shape have conventionally been known, with various methods for the measuring proposed. The proposed methods include: stereoscopic imaging based on a stereoscopic view with both left and right eyes; phase shift by patterned illumination using a sinusoidal pattern and the like; and Time of Flight (TOF) based on time measurement for reflected light.

The stereoscopic imaging can be achieved with a simple mechanism with a stereoscopic optical system used for an imaging system, and thus requires no special illumination mechanisms or illumination control, and also requires no advanced signal processing. Thus, this technique can be suitably implemented in a small space and thus is advantageous in an imaging system that has been progressively downsized recently. For example, the technique can be applied to an end of an endoscope apparatus, to a visual sensor in a small robot, and for various other needs. Such an application is likely to require not only a highly accurate measurement function but also a normal observation function with high image quality. Thus, to ensure a sufficient resolution, it is a common practice to form parallax images on a common image sensor instead of using separate image sensors. The basic idea of the stereoscopic imaging is to obtain a distance to an object based on an amount of parallax between left and right images. If the left and right images fail to be separately formed on the common image sensor, the amount of parallax cannot be detected, and thus the distance information cannot be obtained.

JP-A-2014-28008 discloses an example of a method of separately forming left and right images. Specifically, switching between left and right imaging optical paths is performed along time with a mechanical shutter, so that the left and the right images are obtained. In this method, white light may be used for illumination, for example.

The left and the right images, separately obtained by the method according to JP-A-2014-28008 in a time division manner, can each be used as an observation image.

SUMMARY

According to one aspect of the invention, there is provided an imaging device comprising: an image sensor;
an optical system forming an image of an object on the image sensor; and
a processor,
the optical system switching between a first state of capturing an image of the object with a single pupil and a second state of capturing an image of the object with two pupils,
the processor being configured to implement generating a simulative phase difference image from a first captured image captured with the image sensor in the first state, and executing matching processing of comparing the simulative phase difference image with a second capture image captured with the image sensor in the second state to detect a phase difference between an image formed with one of the two pupils and an image formed with another one of the two pupils.

According to another aspect of the invention, there is provided an endoscope apparatus comprising the above imaging device.

According to another aspect of the invention, there is provided an imaging method comprising:
switching a state of an optical system between a first state in which the optical system forms an image of an object on an image sensor with one pupil and a second state in which the optical system forms the image of the object on the image sensor with two pupils,
generating a simulative phase difference image from a first captured image captured with the image sensor in the first state,
executing matching processing to compare the simulative phase difference image with a second captured image captured with the image sensor in the second state, and
detecting a phase difference between an image formed with one of the two pupils and an image formed with another one of the two pupils.

DESCRIPTION OF EXEMPLARY EMBODIMENTS

Figure 1:
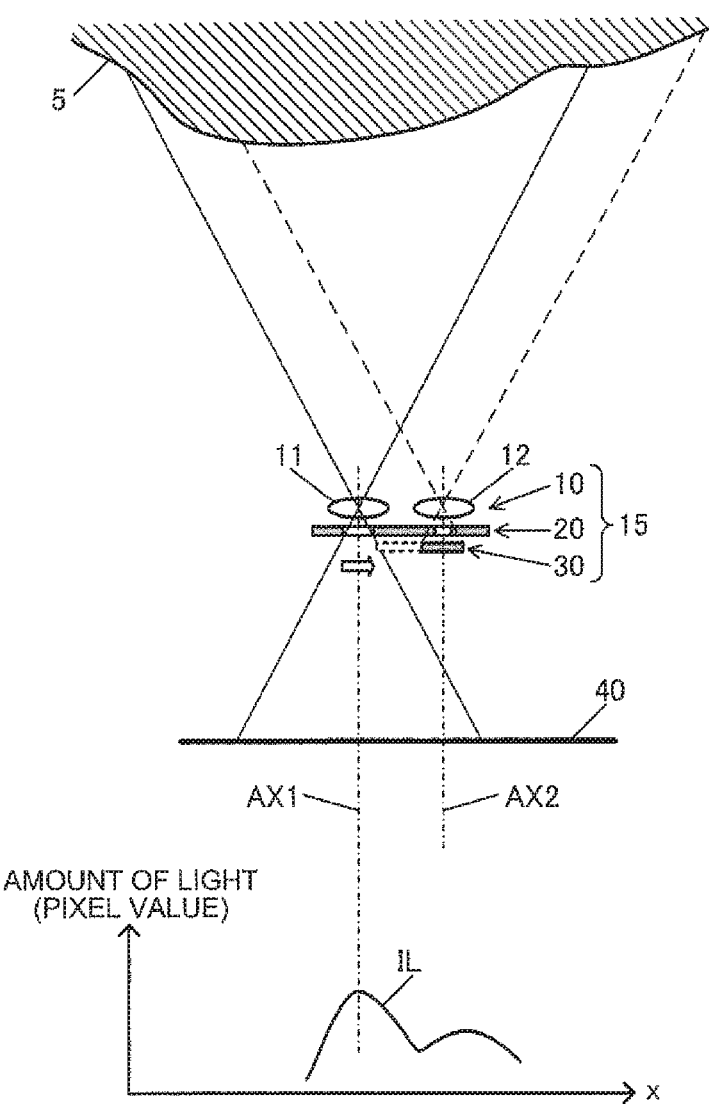
FIG. 1 illustrates an example of a basic configuration of an imaging section of an endoscope apparatus.

Some aspects of the present invention can provide an imaging device, an endoscope apparatus, an imaging method with which a capturing of high resolution image of stereoscopic measurement can both be achieved.

According to one embodiment of the invention, there is provided an imaging device comprising: an image sensor;

an optical system forming an image of an object on the image sensor; and a processor, the optical system switching between a first state of capturing an image of the object with a single pupil and a second state of capturing an image of the object with two pupils, the processor being configured to implement generating a simulative phase difference image from a first captured image captured with the image sensor in the first state, and executing matching processing of comparing the simulative phase difference image with a second capture image captured with the image sensor in the second state to detect a phase difference between an image formed with one of the two pupils and an image formed with another one of the two pupils.

According to one aspect of the present embodiment, the simulative phase difference image is generated from the first captured image obtained with a single pupil and the matching processing is executed to compare the simulative phase difference image with the second captured image captured with two pupils to detect the phase difference. Thus, the stereoscopic measurement can be performed with a phase difference detected from the second captured image obtained by superimposing images obtained with two pupils. With this configuration, images obtained with different pupils need not to be formed on different areas of the image sensor, and can be formed in a large area of the image sensor in a superimposed manner, whereby a high resolution image can be captured.

The present embodiment will be described below. The present embodiment described below does not unduly limit the scope of the present invention described in the appended claims. Not all the components described in the present embodiment are required to embody the present invention.

In the description below, an example where the present invention is applied to an industrial endoscope apparatus is described. However, the application of the present invention is not limited to industrial endoscope apparatuses. The present invention may be applied to any three-dimensional measurement device that measures a three-dimensional shape through stereoscopic imaging (a method of acquiring distance information on an object by detecting a phase difference between two images obtained with an imaging system involving parallax), and to any imaging device having a three-dimensional measurement function (such as a medical endoscope apparatus, a microscope, an industrial camera, and a visual function of a robot, for example).

1. Basic Configuration

For example, an examination using an endoscope apparatus is performed as follows. A scope is inserted into an examination target to check whether there is an abnormality while capturing normal images. When a portion, such as a defect, to be observed in detail is found, the three-dimensional shape of the portion is measured to determine whether a further examination is required. Thus, the normal observation image is captured with white light. For example, stereoscopic imaging may be performed with white light so that stereoscopic measurement and the image capturing with white light can both be achieved. The stereoscopic imaging using white light requires an image sensor to be divided into left and right regions, and a left image and a right image to be respectively formed on the left and the right regions. Thus, only an image with a low resolution can be obtained. A color-phase difference method may be employed to form the left and the right images on a single region of the image sensor. Unfortunately, this method results in a captured image with color misregistration that is unacceptable as the observation image.

In view of the above, time-division switching (for example, JP-A-2014-28008) is required for forming the left and the right images on the single region of the image sensor with white light. However, relative movement between an imaging system and an object leads to shifting due to the movement between the left and the right images, resulting in inaccurate triangulation. Devices such as endoscope cannot have a camera fixed relative to the object and thus are highly likely to involve motion blur.

With the present embodiment, an observation image with high resolution can be captured with white light, and the stereoscopic measurement in a non-time-division manner, not based on the color-phase difference method, can be performed using captured images based on light that has passed through the left and the right pupils to be incident on the same area of the image sensor. Thus, the problems described above can be solved. The present embodiment enables stereoscopic measurement and a capturing of an observation image to be performed in real time.

An application of the present invention described below includes a device having an imaging system that is not stably positioned (fixed) and having an imaging mechanism too small to use a large image sensor for ensuring a sufficient resolution. A typical example of such a device includes an industrial endoscope. Still the application of the present invention is not limited to such a device, and the present invention can be widely applied to a three-dimensional measurement device directed to high-resolution monitoring and highly accurate measurement.

Figure 2:
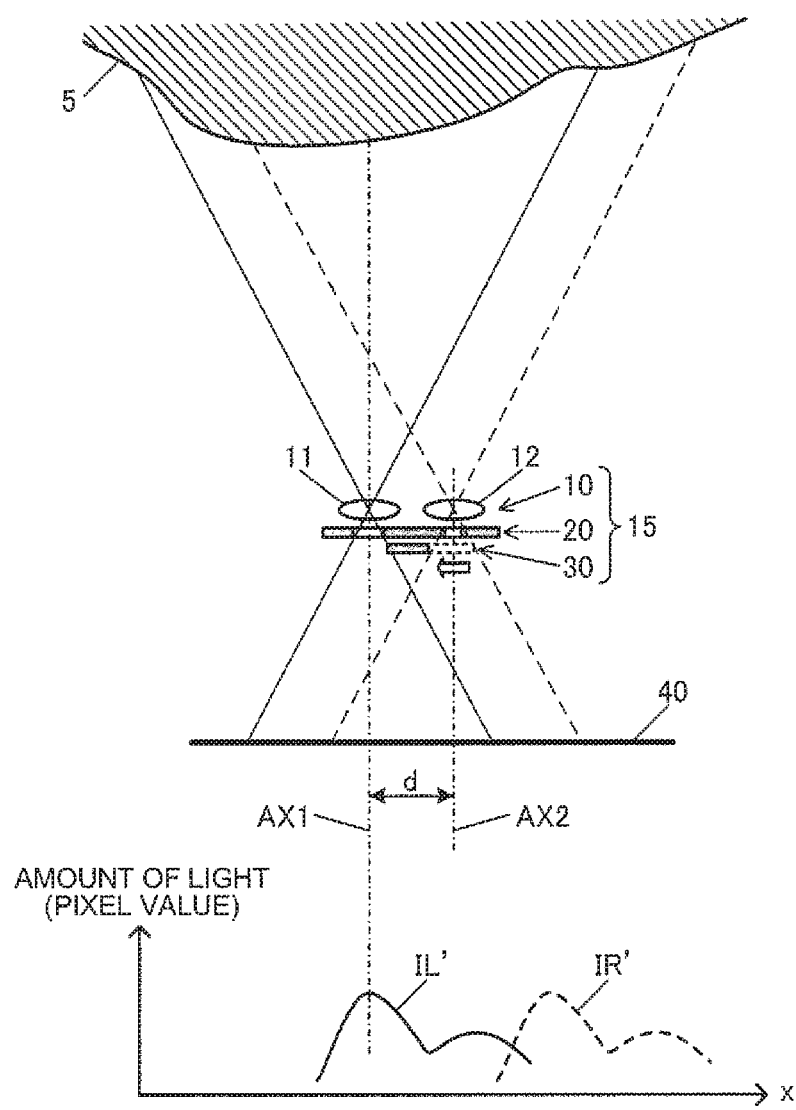
FIG. 2 further illustrates the example of the basic configuration of the imaging section of the endoscope apparatus.

FIG. 1 and FIG. 2 illustrate a basic configuration example of an imaging section of an endoscope apparatus. FIG. 1 and FIG. 2 each include a cross-sectional view of an imaging section as viewed in a lateral direction (on a plane including an optical axis) and a graph illustrating a relationship between an amount of light of an image formed on the image sensor (or a pixel value of an image formed on the image sensor) and a position x. The position x is a position (coordinate) in a direction orthogonal to the optical axis of the imaging optical system, and is a pixel position of the image sensor for example. Although the position is actually defined in a two-dimensional coordinate system, the position is described based on a one-dimensional coordinate system corresponding to a parallax direction in the two dimensional coordinate system. An illumination mechanism is omitted in the figures used in the description below.

The endoscope apparatus according to the present embodiment includes an optical system 15 (optical device) and an image sensor 40. The optical system 15 includes an imaging optical system 10, a movable mask 30 (first mask), and a fixed mask 20 (second mask).

The imaging optical system 10 includes a left-eye imaging system 11 (first imaging optical system) and a right-eye imaging system 12 (second imaging optical system) forming a stereoscopic optical system. For example, each of the left- and the right-eye imaging optical systems includes one or a plurality of lenses, and forms an image of an object entirely over (or on a major part of) the pixel array of the image sensor 40. For example, image circles of the left- and the right-eye imaging optical systems largely overlap. The pixel array of the image sensor is placed within this overlapping area. In the figure, d represents a distance between an optical axis AX1 of the left-eye imaging system 11 and an optical axis AX2 of the right-eye imaging system 12, serving as a baseline length in the stereoscopic measurement.

For example, the image sensor 40 includes a color filter with RGB Bayerpattern. However, this should not be construed in a limiting sense. For example, a complementary color filter or the like may be provided.

For example, the fixed mask 20 and the movable mask 30 are disposed at a pupil position of the imaging optical system 10. The fixed mask 20 is fixed with respect to the imaging optical system 10, whereas the movable mask 30 can have the position switched on a plane orthogonal to the optical axes AX1 and AX2. Thus, the movable mask 30 can achieve high speed switching between a first state illustrated in FIG. 1, corresponding to the observation mode (monitoring mode, first mode, first state), and in a second state, corresponding to a stereoscopic measurement mode (stereoscopic measurement mode, second state, second mode) illustrated in FIG. 2. The movable mask 30 is a light shielding section (light shielding member). The size of the movable mask 30 is set in such a manner that one of two stop holes of the fixed mask 20 can be covered with the light shielding section in the first mode. FIG. 1 and FIG. 2 each illustrate a configuration where the movable mask 30 is disposed more on the image side than the fixed mask 20. Alternatively, the movable mask 30 may be disposed more on the object side than the fixed mask 20.

One of two optical paths, that is, one of left- and right-eye optical paths or both is selected as an imaging optical path of the imaging optical system 10 with the fixed mask 20 and the movable mask 30.

FIG. 1 illustrates a state (observation mode) for obtained a normal observation image. In this state, the right-eye optical path is blocked (shielded) with the movable mask 30 and only the left-eye optical path corresponding to the stop hole of the fixed mask 20 is open. Thus, an image IL formed on the image sensor 40 is obtained with the left-eye imaging system 11 only, whereby a normal captured image (obtained with a single optical system and white light) is obtained.

FIG. 2 illustrates a state (stereoscopic measurement mode) for simultaneously obtaining left and right stereoscopic images. In this state, the left and the right optical paths are open with the movable mask 30, and an image (double image) as a result of superimposing a left pupil image IL' with a right pupil image IR' is obtained. The left pupil image IL' and the right pupil image IR' are each a white light image. The white light image is an image captured based on spectral characteristics of a color filter of an image sensor, and includes a red color component, a green color component, and a blue color component. The color filter may have an infrared range. In such a case, the components of the colors of the image may each include an infrared component.

2. Fixed Mask and Movable Mask

Figure 3:
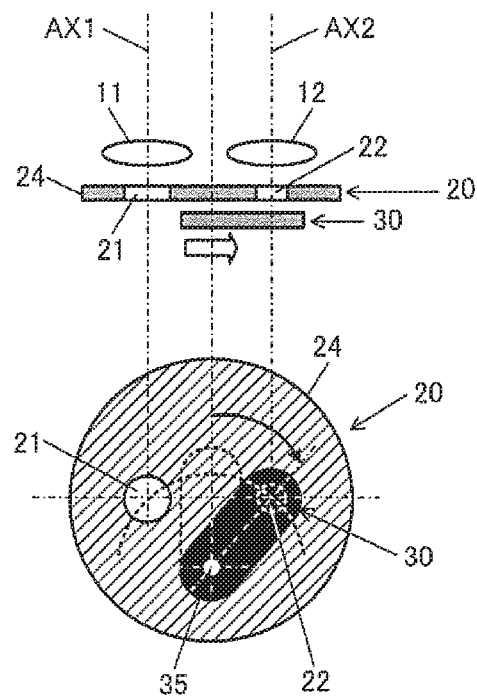
FIG. 3 illustrates an example of a detailed configuration of a fixed mask and a movable mask.
Figure 4:
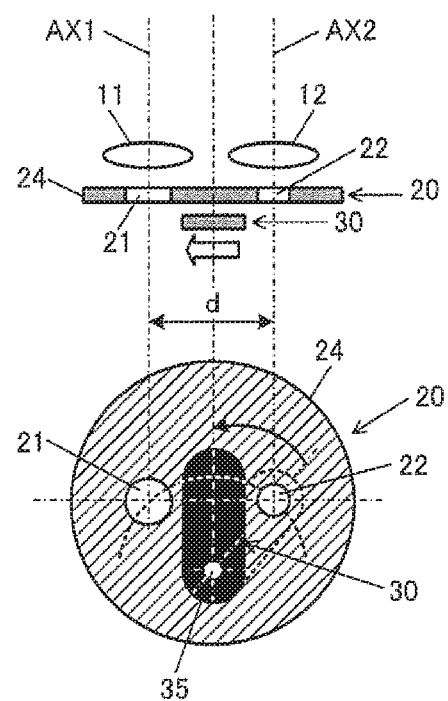
FIG. 4 further illustrates the example of the detailed configuration of the fixed mask and the movable mask.

FIG. 3 and FIG. 4 illustrate a detailed configuration example of the fixed mask 20 and the movable mask 30. FIG. 3 and FIG. 4 each include a cross-sectional view of the imaging optical system 10, the fixed mask 20, and the movable mask 30, and a diagram illustrating the fixed mask 20 and the movable mask 30 as viewed in the optical axis direction (a back view as viewed from the image side).

The left-pupil optical path of the fixed mask 20 has a stop hole 21. The right-pupil optical path has a stop hole 22. The stop holes 21 and 22 are formed on a light shielding section 24 (shielding member), and are each in an open state (through hole). The stop holes 21 and 22 are arranged on the same circle with the rotational shaft 35 at the center, for example. The stop holes 21 and 22 have the centers (the center of a circle for example) respectively matching the optical axes AX1 and AX2. The light shielding section 24 is a plate-shaped member provided to be orthogonal with respect to the optical axes AX1 and AX2 for example, to shield a casing, including the imaging optical system 10, in front view (or back view) of the casing.

The movable mask 30 includes a light shielding section with no stop hole. The light shielding section is connected to a rotational shaft 35 orthogonal to the optical axes AX1 and AX2, and is a plate-shaped member provided to be orthogonal to the optical axes AX1 and AX2 for example. The light shielding section has a form of a bar (with one end connected to the rotational shaft 35). However, this should not be construed in a limiting sense, and any shape may be employed as long as the states illustrated in FIG. 3 and FIG. 4 can be achieved.

The movable mask 30 rotates about the rotational shaft 35 by a predetermined angle in the direction orthogonal to the optical axes AX1 and AX2. For example, this rotational motion can be implemented with a piezoelectric element, a motor, or the like. In the observation mode illustrated in FIG. 3, the left-eye optical path (stop hole 21) of the fixed mask 20 is in an open state and the right-eye optical path (stop hole 22) is in a shielded state, as a result of the rotation of the movable mask 30 toward the right-eye side by the predetermined angle. In the stereoscopic measurement mode illustrated in FIG. 4, the movable mask 30 is returned to a state with a rotational angle of 0 degrees. As a result, the left- and the right-pupil optical paths (stop holes 21 and 22) of the fixed mask 20 are in the open state.

The stop holes 21 and 22 are holes with sizes corresponding to the depth of field required for capturing an observation image (for example, circular holes with a size defined with a diameter). FIG. 1 to FIG. 4 illustrate a case where an area φL of the stop hole 21 and an area φR of the stop hole 22 are different from each other. Note that the area φL of the stop hole 21 and the area φR of the stop hole 22 may be the same. When the areas are different, the stop hole 22 is smaller than the stop hole 21 for example. In FIG. 3 and FIG. 4, φL>φR holds true. However, this should not be construed in a limiting sense, and a configuration satisfying φL<φR may be employed.

In the description above, the two states are established with the movable mask 30 rotated by the predetermined angle about the shaft. However, this should not be construed in a limiting sense. For example, the two states may be established with a sliding motion of the movable mask 30. For example, the rotational motion or the sliding motion can be implemented with a magnet mechanism, a piezoelectric mechanism, or the like that may be appropriately selected to achieve a high speed motion and high resistance.

3. Endoscope Apparatus

Figure 5:
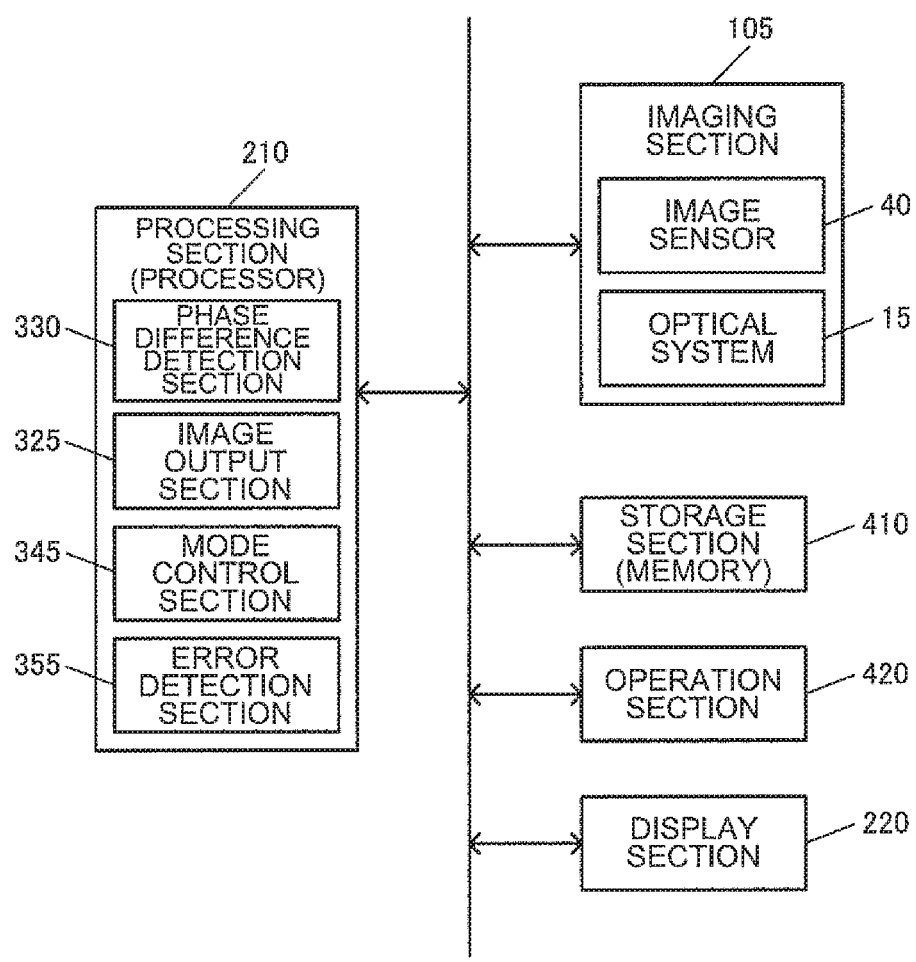
FIG. 5 illustrates an example of a configuration of the endoscope apparatus.

FIG. 5 illustrates a configuration example of an endoscope apparatus (an imaging device in a broad sense) according to the present embodiment. The endoscope apparatus includes a processing section 210 (processing device, processor), an imaging section 105, a storage section 410 (memory), an operation section 420 (operation device), and a display section 220 (display device, display). The processing section 210 includes a phase difference detection section 330 and an image output section 325.

The processing section 210 controls the sections of the endoscope apparatus and executes various types of information processing including image processing for example. The processing section 210 includes the phase difference detection section 330, the image output section 325, and a mode control section 345. For example, the storage section 410 stores therein image data on an image captured with the imaging section 105, setting data on the endoscope apparatus, and the like. Alternatively, the storage section 410 is used as a temporally storage memory (working memory) for the processing section 210. The imaging section 105 captures an image (movie or a still image). The imaging section 105 includes the image sensor 40 and the optical system 15. The imaging section 105 may further include a driving device that drives a focus mechanism of the optical system 15. The operation section 420 is an input device enabling the user to operate the imaging device, and may include a button, a lever, a rotation ring, a mouse, a keyboard, a touch panel, and the like. The display section 220 displays an image that has been captured with the imaging section 105 and an image that has been processed by the processing section 210. Examples of a display section 400 include a liquid crystal display device, an electro-luminescence (EL) display device, and the like.

A configuration and an operation of the endoscope apparatus according to the present embodiment are described in detail below.

The optical system 15 switches between the first state and the second state. In the first state, an image of an object 5 is formed with a single pupil. In the second state, an image of the object is formed with two pupils. The phase difference detection section 330 generates a simulative phase difference image from a first captured image IL(x) captured with the image sensor 40 in the first state. The phase difference detection section 330 executes matching processing to compare the simulative phase difference image with a second captured image ILR'(x) captured with the image sensor in the second state. Then, the phase difference detection section 330 detects a phase difference between an image formed with one of the two pupils and an image formed with the other one of the pupils.

The first state corresponds to an observation image acquisition state (observation mode) in FIG. 1 and FIG. 3. The second state corresponds to a measurement image acquisition state (stereoscopic measurement mode) in FIG. 2 and FIG. 4. A single pupil in the first state corresponds to the stop hole 21 of the fixed mask 20. The two pupils in the second state correspond to the stop holes 21 and 22 in the fixed mask 20. In FIG. 1 to FIG. 4, the two pupils are illustrated as left and right pupils. Note that the direction in which the two pupils are separated from each other is not limited to the left and right direction.

The simulative phase difference image (combined image, simulated image, simulated phase difference image) is an image, simulating the second captured image ILR'(x), obtained by combining the first captured image IL(x) with an image as a result of providing a simulative phase difference to the first captured image IL(x) to shift a position. Providing the simulative (intentional) phase difference corresponds to providing a variable corresponding to an appropriate phase difference and shifting a position x by an amount corresponding to the variable. This corresponds to converting the first captured image IL(x) into an image IL(x−s). In the matching processing, a phase difference with which the images match is searched for while changing the simulative phase difference to be provided. A detail description on such a method of detecting the phase difference will be given with reference to FIG. 6, FIG. 7, and FIG. 18 to FIG. 20. In the detailed description, the simulative phase difference image corresponds to an image ILR(x,s) in Formula (2) described later, an image ILR(x,δ,s) in Formula (4) described later, and a vector NCV in Formula (26) described later. The simulative phase difference to be provided corresponds to s and the phase difference detected corresponds to s'(xL).

In the present embodiment, the simulative phase difference image is generated from the first captured image IL(x) obtained with a single pupil. The matching processing is executed to compare the simulative phase difference image with the second captured image ILR'(x) obtained with two pupils, so that the phase difference is detected. The second captured image ILR'(x) is obtained by superimposing images, obtained with two pupils at once, with each other. This means that the images are not obtained with the pupils in a time division manner, whereby the phase difference is not affected by movement of the object or the imaging system. Thus, an accurate phase difference (an object distance) unaffected by the movement of the imaging system can be detected. The matching processing is executed with the simulative phase difference image, simulating the second captured image ILR'(x), generated from the first captured image IL(x). Thus, the phase difference can be detected from the second captured image ILR'(x) obtained by superimposing the images, obtained with the two pupils, with each other. With the phase difference being capable of being detected from the superimposed image, a color-phase difference method needs not to be employed, whereby the stereoscopic measurement can be implemented with white light. The first captured image IL(x) captured with a single pupil can be provided as an observation image. Thus, the stereoscopic measurement and provision of the observation image can both be achieved.

The endoscope apparatus (imaging device) according to the present embodiment may have the configuration described below. Specifically, the endoscope apparatus according to the present embodiment includes the image sensor 40, the optical system 15, a memory (storage section 410) that stores information (for example, a program and various types of data), and a processor (a processing section 210, a processor including hardware) that operates based on the information stored in the memory. The processor executes phase difference detection processing including: generating the simulative phase difference image from the first captured image IL(x); executing the matching processing to compare the simulative phase difference image with the second captured image ILR'(x); and detecting a phase difference between an image formed with one of the two pupils and an image formed with the other one of the two pupils.

For example, the function of each section may be implemented by the processor or may be implemented by integrated hardware. For example, the processor may include hardware, and the hardware may include at least one of a circuit that processes a digital signal and a circuit that processes an analog signal. For example, the processor may include one or more circuit devices (e.g., IC), and one or more circuit elements (e.g., resistor or capacitor) that are mounted on a circuit board. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an ASIC. The processor may include an amplifier circuit, a filter circuit, and the like that process an analog signal. The memory may be a semiconductor memory (e.g., SRAM or DRAM), or may be a register. The memory may be a magnetic storage device such as a hard disk drive (HDD), or may be an optical storage device such as an optical disc device. For example, the memory stores a computer-readable instruction, and the function of each section of the processing section 210 is implemented by causing the processor to perform the instruction. The sections of the processing section 210 includes a phase difference detection section 330, an image output section 325, a mode control section 345, and an error detection section 355 in FIG. 5. The sections of the processing section 210 further includes an image selection section 310, a color image generating section 320, the phase difference detection section 330, a movable mask control section 340, a movable mask position detection section 350, a distance information calculation section 360, and a three-dimensional information generating section 370 in FIG. 9. The instruction may be an instruction set that is included in a program, or may be an instruction that instructs the hardware circuit included in the processor to operate.

For example, operations according to the present embodiment are implemented as follows. The processor performs control to switch the optical system 15 between the first state and the second state. The first captured image IL(x) and the second captured image ILR'(x) captured with the image sensor 40 are stored in the memory (storage section 410). The processor reads the first captured image IL(x) from the memory to generate a simulative phase difference image, and stores the simulative phase difference image in the memory. The processor reads the second captured image ILR'(x) and the simulative phase difference image from the memory, executes the matching processing to compare the images to detect the phase difference, and stores the phase difference thus detected in the memory.

The sections of the processing section 210 according to the present embodiment are implemented as modules of a program operating on the processor. For example, the phase difference detection section 330 is implemented as a phase difference detection module that generates the simulative phase difference image from the first captured image IL(x), and executes the matching processing to compare the second captured image ILR'(x) with the simulative phase difference image to detect the phase difference between an image formed with one of the two pupils and an image formed with the other one of the two pupils.

In the present embodiment, the phase difference detection section 330 generates a first simulative pupil image and a second simulative pupil image, respectively formed with one and the other one of the pupils, from the first captured image IL(x). The phase difference detection section 330 generates the simulative phase difference image through processing of adding together the first simulative pupil image and the second simulative pupil image shifted from each other by a shifted amount corresponding to the phase difference. The phase difference detection section 330 detects the phase difference by executing the matching processing while changing the shifting amount.

The first simulative pupil image (first pupil image, first simulated pupil image) is an image simulating an image formed with one of the pupils, as a part of the second captured image ILR'(x), based on the first captured image IL(x). The second simulative pupil image (second pupil image, second simulated pupil image) is an image simulating an image formed with the other one of the pupils, as a part of the second captured image ILR'(x), based on the first captured image IL(x). Simulating the pupil image corresponds to providing the variable corresponding to an appropriate phase difference and shifting relative positions of the first simulative pupil image and the second simulative pupil image by an amount corresponding to the variable. In a method described later with reference to FIG. 6, the first and the second simulative pupil images respectively correspond to the image IL(x) and an image IL(x,s) in Formula (1) described later. The simulative phase difference image ILR(x,s) is obtained through processing of adding the first and the second simulative pupil images together as in Formula (2) described later. In a method described later with reference to FIG. 7, the first and the second simulative pupil images respectively correspond to images IL(x,δ) and IL(x,δ,s) in Formula (3) described later. The simulative phase difference image ILR(x,δ,s) is obtained through processing of adding the first and the second simulative pupil images as in Formula (4) described later. In a method described later with reference to FIG. 18 to FIG. 20, the first and the second simulative pupil images respectively correspond to vectors RL and RR in Formula (21) described later. The simulative phase difference image (vector NCV) is obtained through processing of adding the first and the second simulative pupil images (vectors RL and RR) as in Formula (26) described later.

In the present embodiment, the images formed with the two pupils are generated from the first captured image IL(x), and the simulative phase difference image is generated through the processing of adding the images together. Thus, the image simulating the second captured image ILR'(x) based on a certain assumed phase difference (shifting amount) is generated. Then, through the matching processing executed while changing the assumed phase difference, the phase difference for the second captured image ILR'(x), obtained by superimposing the images, obtained with the two pupils, with each other, can be searched for and determined.

In the present embodiment, the two pupils of the optical system 15 have different sizes.

The size of the pupil corresponds to an area of an opening of the pupil. For example, the size of the pupil may be directly represented by the area of the opening, or may be represented by a parameter of a shape of the opening that can be used instead of the area. For example, when the opening has a shape of a circle, the size of the pupil may be represented by a diameter of the circle.

The matching processing is based on local area comparison that may result in a high pseudo correlation for similar images (waveforms). In view of this, the present embodiment features the two pupils of different sizes. Thus, captured images obtained with the two pupils are different from each other in brightness, whereby the second captured image ILR'(x) can be characterized. This ensures a lower risk of the matching processing resulting in pseudo correlation, whereby more accurate phase difference detection can be achieved.

As described later with reference to FIG. 12 to FIG. 15, the imaging optical system 10 of the optical system 15 may be a monocular optical system. In such a configuration, whether the phase difference is of a positive value or a negative value is determined based on a focus position (whether the focus position is shifted forward or rearward) as in Formula (17) described later. With the configuration where the captured images obtained with the pupils have the same brightness, the second captured image ILR'(x) is the same regardless of whether the phase difference is of a positive or a negative value if the absolute value of the phase difference is the same. Thus, the phase difference cannot be detected. In view of this, with the present embodiment, the captured images obtained with the pupils are different from each other in brightness, so that the phase difference can be accurately detected with the monocular imaging optical system 10.

When the imaging optical system 10 is a stereoscopic optical system as illustrated in FIG. 1 to FIG. 4, the optical system 15 may have two pupils of the same size.

In the present embodiment, the phase difference detection section 330 executes gain adjustment, based on different sizes of the two pupils, on the first captured image IL(x) to generate the first simulative pupil image corresponding to an image formed with one of the pupils and the second simulative pupil image corresponding to an image formed with the other one of the pupils. The phase difference detection section 330 generates the simulative phase difference image through the processing of adding together the first simulative pupil image and the second simulative pupil image shifted from each other by an amount corresponding to the phase difference. Then, the phase difference detection section 330 detects the phase difference by executing the matching processing while changing the shifting amount.

In the method described later with reference to FIG. 6, the gain adjustment corresponds to processing of multiplying the image IL(x−s) by a coefficient (φR/φL) as in Formula (1) described later. In the method described later with reference to FIG. 7, the gain adjustment corresponds to processing of multiplying the image IL(x−δ−s) by the coefficient (φR/φL) as in Formula (3) described later. The coefficient (φR/φL) is an area ratio between the openings of the pupils. In the method described later with reference to FIG. 18 to FIG. 20, the gain adjustment corresponds to processing of multiplying vectors VL and VR by coefficients gL and gR as in Formula (26) described later. The coefficients gL and gR represent a ratio between sizes of the vectors (brightness of the images) as can be seen in Formula (25) described later. The ratio is related to the area ratio between the openings of the pupils (the ratio may be substantially the same as the area ratio, but is not necessarily the same as the area ratio).

In the present embodiment, the simulative phase difference image can be appropriately generated with the two pupils of the optical system 15 with difference sizes. Specifically, the gain adjustment based on the sizes of the openings is executed on the first captured image IL(x) that is captured with a single pupil, so that the simulative phase difference image simulating the second captured image ILR'(x) captured with two pupils with openings with different sizes can be generated.

In the present embodiment, the phase difference detection section 330 detects a motion amount due to an object moving between the first captured image IL(x) and the second captured image ILR'(x), based on the first captured image IL(x) and the second captured image ILR'(x).

The object movement is a movement (shifting) of an imaging position of the object between two images captured at different timings. The object movement is caused by one of a movement (shifting) of the object, a movement (shifting) of the imaging system, or both.

The first captured image IL(x) and the second captured image ILR'(x) are captured in a time division manner, and thus the phase difference might not be accurately detectable when the object movement occurs between the image capturing timings. In the present embodiment, the phase difference can be detected without being affected by the object movement, with the motion amount between the first captured image IL(x) and the second captured image ILR'(x) further detected. The images are simultaneously obtained with the two pupils to be the second captured image ILR'(x) including information on the phase difference not affected by the movement. Thus, the object movement and the phase difference can be separately detected.

In the present embodiment, the phase difference detection section 330 generates the simulative phase difference image through the processing of adding together the first simulative pupil image and the second simulative pupil image, shifted from each other by a first shifting amount corresponding to the phase difference and by a second shifting amount corresponding to the motion amount. The phase difference detection section 330 detects the phase difference and the motion amount by executing the matching processing with the first shifting amount and the second shifting amount changed independently from each other.

In the methods described later with reference to FIG. 7 and FIG. 18 to FIG. 20, s and δ respectively correspond to the first shifting amount (phased difference) and the second shifting amount (motion amount), for generating the simulative phase difference image. In the methods, s'(xL) and δ'(xL) respectively represent the phase difference detected by the matching processing and the motion amount.

In the present embodiment, the images obtained with the two pupils are generated from the first captured image IL(x), and the simulative phase difference image is generated through the processing of adding the images together. Thus, an image simulating the second captured image ILR'(x) based on a certain assumed phase difference (first shifting amount) and a certain assumed motion amount (second shifting amount). The information on the phase difference in the second captured image ILR'(x) can be extracted and the motion amount between the first captured image IL(x) and the second captured image ILR'(x) can be detected by executing the matching processing by changing the assumed phase difference and the assumed motion amount.

In the present embodiment, the optical system 15 is set to be in the first state in an n-th frame (n is an integer) and is set to be in the second state in an n+1-th frame to an n+j-th frame (j is an integer equal to or larger than 2) after the n-th frame. The phase difference detection section 330 detects the phase difference for j times based on the first captured image IL(x) captured in the n-th frame and the second captured image ILR'(x) captured in an n+i-th frame (i is an integer that is equal to or larger than 1 and is equal to or smaller than j), and executes processing of averaging the j phase differences.

Figure 11:
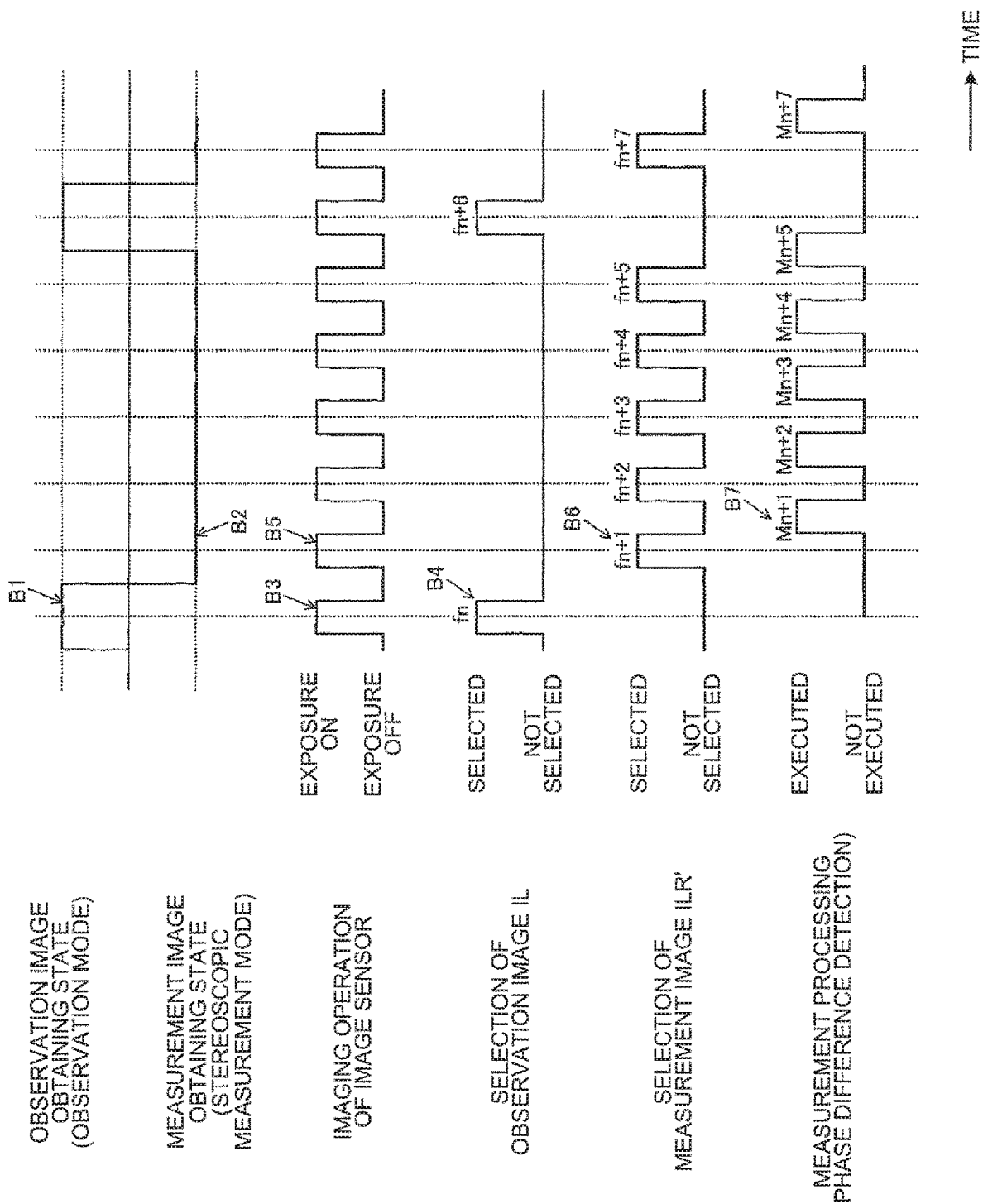
FIG. 11 illustrates a second sequence of operations in movie capturing.

This processing is described in detail later with reference to FIG. 11. In FIG. 11, a final phase difference s'(xL) is obtained by the processing of averaging the j phase differences with Formula (11) described later where j is 5.

Considering the object movement, logically, the time interval between the image capturing in the first state and the image capturing in the second state should be short as much as possible. However, in the present embodiment, the motion amount and the phase difference can be detected independently from each other. This allows a certain length of time interval to be set between the image capturing in the first state and the image capturing in the second state without compromising the accuracy of the phase difference detection. Thus, the final phase difference can be obtained by averaging a plurality of phase differences obtained by sequentially capturing images for a plurality of times in the second state after a single image has been captured in the first state. The processing of averaging the plurality of phase differences ensures more accurate phase difference detection.

In the present embodiment, the endoscope apparatus includes the image output section 325 that outputs an observation image based on the first captured image IL(x).

In the present embodiment, the stereoscopic measurement based on the first captured image IL(x) and the second captured image ILR'(x) and the output of the observation image based on the first captured image IL(x) can both be achieved. This ensures capturing of the observation image and the stereoscopic measurement for an object in the image to be substantially simultaneously implemented. As will be described later with reference to FIG. 10 and FIG. 11, this processing may be applied to a case where a movie is captured so that capturing of the observation image and stereoscopic measurement can be implemented substantially in real-time.

In the present embodiment, the optical system 15 includes the fixed mask 20 including first and second openings and the movable mask 30 that is movable relative to the fixed mask 20. In the first state, the optical system 15 forms an image of the object 5 with the first opening serving as the single pupil, with the movable mask 30 not shielding the first opening and shielding the second opening. In the second state, the optical system 15 forms the image of the object 5 with the first opening and the second opening serving as the two pupils, with the movable mask 30 shielding none of the first opening and the second opening.

In FIG. 3 and FIG. 4, the first opening corresponds to the stop hole 21 and the second opening corresponds to the stop hole 22. The mask is a member or a component shielding light incident on the mask. The fixed mask 20 according to the present embodiment has a light shielding section 24 shielding light and the stop holes 21 and 22 transmitting light. The movable mask 30 is formed of a light shielding section with no opening, and shields light.

In the present embodiment, the first state of forming the image of the object with a single pupil can be established with the movable mask 30 shielding the second opening without shielding the first opening. The second state of forming the image of the object with two pupils can be established with the movable mask 30 not shielding the first and the second openings.

In the present embodiment, the second opening is smaller than the first opening on the fixed mask 20.

In the present embodiment, two pupils with different sizes can be implemented. For example, the size of an opening is represented by a parameter of the shape of the opening that can be used instead of the area. For example, when the opening has a shape of a circle, the size is represented by a diameter of the circle. Alternatively, the area of the opening may be directly used as the size of the opening.

In the present embodiment, the fixed mask 20 and the movable mask 30 may be configured as follows. Specifically, the fixed mask includes an opening. In the first state, the movable mask 30 does not split an opening (sets the opening to be in an open state), and the optical system 15 forms an image of the object 5 with the opening that is not split serving as the single pupil. In the second state, the movable mask 30 splits the opening into a first split opening and a second split opening smaller than the first split opening. The optical system 15 forms an image of the object 5 with the first and the second split openings servings as the two pupils.

Figure 16:
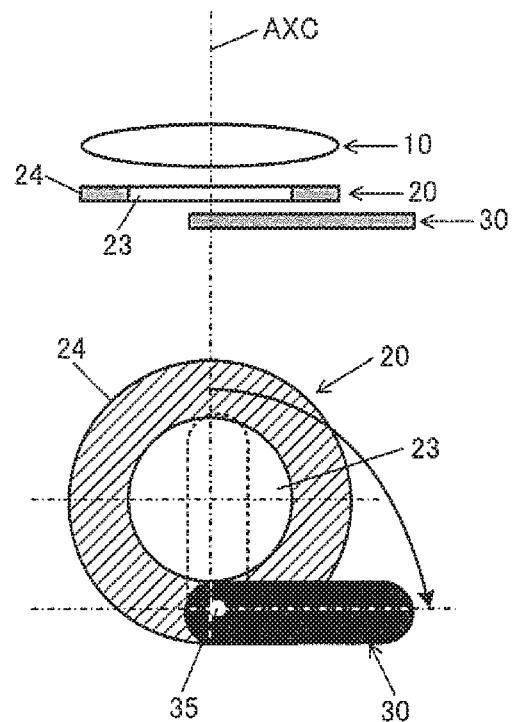
FIG. 16 illustrates the third detail configuration example of the fixed mask and the movable mask.
Figure 17:
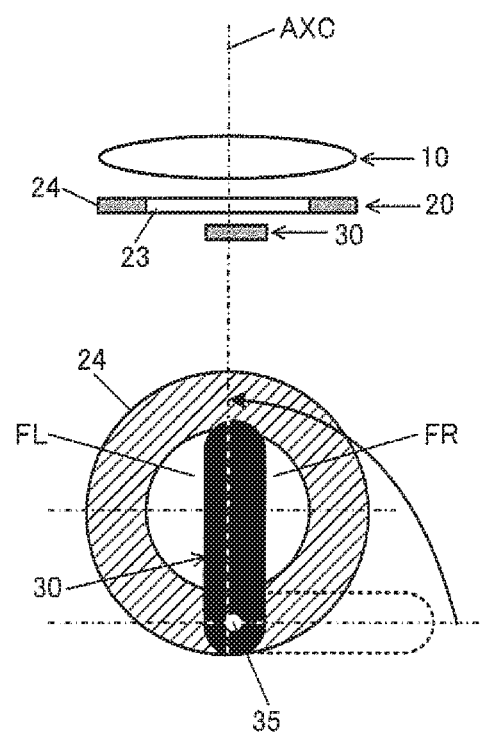
FIG. 17 illustrates the third detail configuration example of the fixed mask and the movable mask.

This configuration is described in detail with reference to FIG. 16 and FIG. 17. In FIG. 16 and FIG. 17, the opening of the fixed mask 20 corresponds to a stop hole 23 and the first and the second split openings respectively correspond to holes FL and FR.

In the present embodiment, the first state for forming an image of an object with a single pupil can be established with the movable mask 30 not splitting the opening of the fixed mask 20. The second state of forming an image of an object with two pupils can be established with the movable mask 30 splitting the opening of the fixed mask 20 into the first split opening and the second split opening.

In the present embodiment, the endoscope apparatus includes the mode control section 345 that performs control to switch between a first mode (observation mode) of setting the optical system 15 to be in the first state and a second mode (stereoscopic measurement mode) of setting the optical system 15 to be in the second state.

The mode control section 345 is described in detail with reference to FIG. 9. The movable mask control section 340 in FIG. 9 corresponds to the mode control section 345.

In the present embodiment, the state of the optical system 15 can be switched between the first state and the second state, through mode setting by the mode control section 345. The phase difference detection section 330 can determine whether the captured image is the first captured image or is the second captured image based on mode information from the mode control section 345.

In the present embodiment, the error detection section 355 is provided to detect at least one of the optical system 15 set to be in the first state under the first mode and the optical system 15 set to be in the second state under the second mode, based on the image IL(x) captured under the first mode and the image ILR'(x) captured under the second mode.

The error detection section 355 is described in detail with reference to FIG. 9. The movable mask position detection section 350 in FIG. 9 corresponds to the error detection section 355.

The optical system 15 is configured to be switched between the first and the second states, and includes a movable section (movable mask 30). When such a movable section is used, a possibility of an erroneous operation of the movable section needs to be taken into consideration. In the present embodiment, whether or not appropriate switching between the first and the second states is achieved can be detected from the image. When an error is detected, the image capturing may be stopped or the operation of the movable section may be corrected, for example. For example, it is determined that the normal state has been restored when the error is no longer detected as a result of temporally stopping and then resuming the operation of the movable section.

4. Method of Detecting Phase Difference

A phase difference s between the left pupil image IL' and the right pupil image IR' needs to be detected to obtain the distance to the object. The image obtained in the stereoscopic measurement mode described above is formed by superimposing the left pupil image IL' and the right pupil image IR'. Thus, the phase difference s cannot be detected by using this image only. Thus, the phase difference s is obtained by using the image IL obtained under the observation mode. This method is described below.

Figure 6:
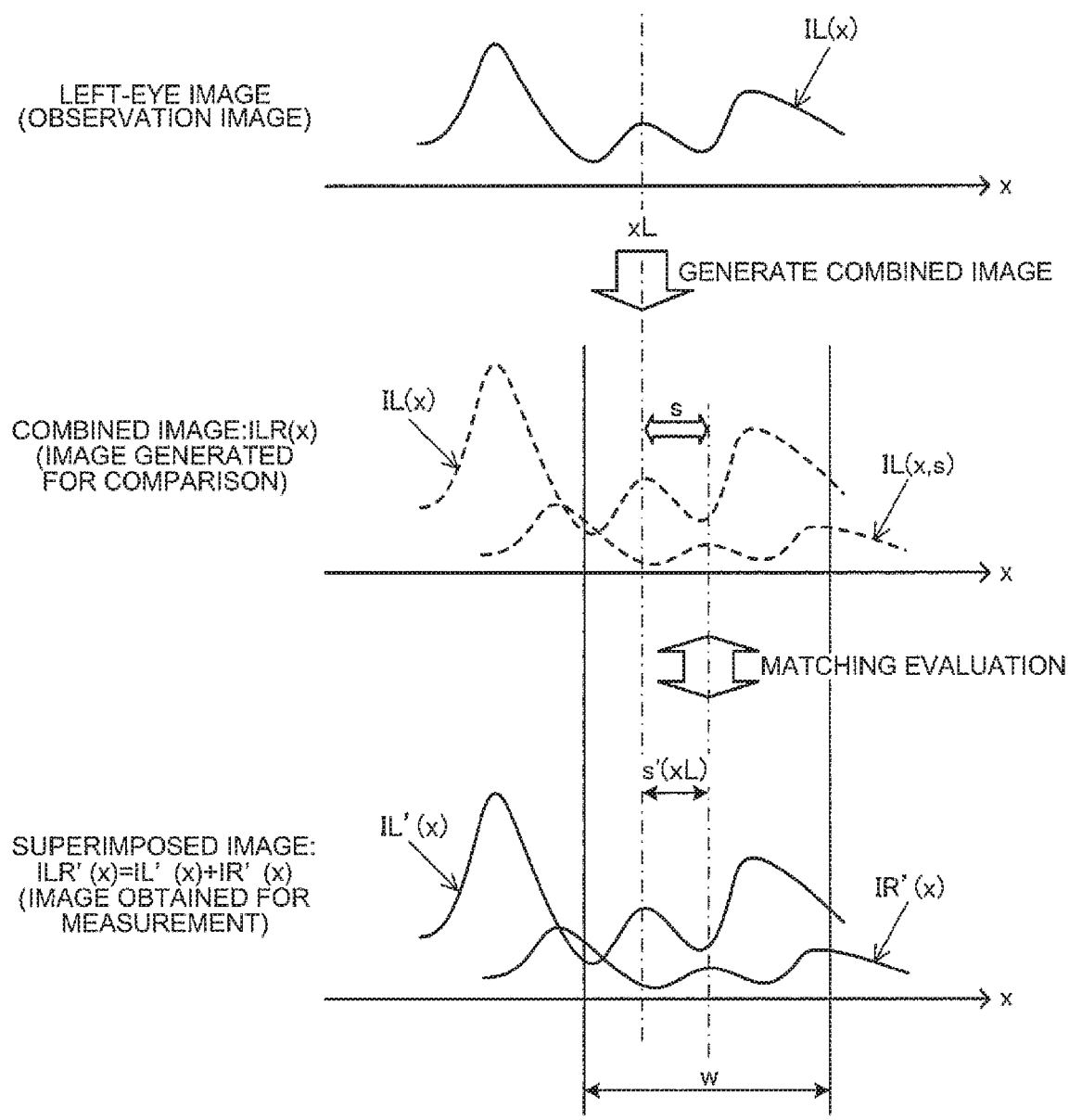
FIG. 6 illustrates a phase difference detection method.

FIG. 6 illustrates a method of detecting the phase difference. The simple description is given by focusing only on an x coordinate and ignoring a y coordinate. Pixel values of the images IL, IL', and IR' are regarded as functions of the x coordinate, and will be referred to as IL(x), IL'(x), and IR'(x), respectively. In the actual stereoscopic measurement mode, a captured image ILR'(x)=[IL'(x)+IR'(x)] is obtained. Still, IL'(x) and IR'(x) are each illustrated as an individual waveform in FIG. 6. In processing of detecting a phase difference, the images IL(x) and ILR'(x) are converted into monochrome images (greyscale images), and the phase difference is detected from the monochrome images, for example.

First of all, the image IL(x−s) is generated by shifting the left pupil image IL(x) for observation by s from a certain coordinate xL. The stop holes 21 and 22 have different sizes. Thus, gain adjustment based on IL(x) is executed on IL(x−s) as in the following Formula (1) using the ratio between the areas φL and φR of the stop holes 21 and 22. An image after the gain adjustment is referred to as IL(x,s).

$$IL(x,s)=(\varphi R/\varphi L)\cdot IL(x-s) \quad (1)$$

The adjustment gain (φR/φL) is for gain matching between the left and the right pupil images. In Formula (1) described above, the gain is set based on an area ratio between the stop holes 21 and 22. However, this should not be construed in a limiting sense, and the optimum gain adjustment may be implemented based on the optical characteristics of an actual imaging system for example.

Next, IL1(x) and IL(x,s) in Formula (1) described above are combined to generate the combined image ILR(x,s) as in Formula (2) described below to be a comparison image for the search. ILR(x,s) is an image obtained by adding together the two images IL(x) (one of which has had the gain adjustment) shifted from each other by the phase difference s.

$$ILR(x,s)=IL(x)+IL(x,s)=IL(x)+(\varphi R/\varphi L)\cdot IL(x-s) \quad (2)$$

Next, matching valuated is performed while changing the shifting amount s to check that matching between the superimposed image ILR'(x)[=IL'(x)+IR'(x)] captured for the measurement and the combined image ILR(x,s) corresponding to each value of the shifting amount s. Then, the shifting amount s providing the highest level of matching is detected to be the phase difference s'(xL) between the left pupil image IL'(x) and the right pupil image IR'(x) at the coordinate xL. In FIG. 6, w represents a range in which comparison to check the similarity is performed in the matching evaluation.

In this method, the images IL(x), IL'(x), and IR'(x) correspond to different points of view but are regarded as being substantially in similar relationship locally. Specifically, in a predetermined section, IL(x) and IL'(x) are regarded as substantially matching, and an image obtained by shifting IL(x) by s and IR'(x) are also regarded as matching. Thus, whether or not ILR(x) and ILR'(x) in the combined state match is checked while changing the search value s. When ILR(x) and ILR'(x) match, IL(x) and IL'(x) are determined to match and IL(x−s) and IR'(x) are determined to match, and s at this point is determined as a phase difference s' to be obtained.

5. Method of Detecting Phase Difference while Taking Movement into Consideration The phase difference s' obtained as described above is obtained under an assumption that images are obtained with no movement between the imaging system and the object, that is, under an assumption that the image IL(x) and the image IL'(x) are at the same position in an imaging plane. However, the left pupil image IL(x) for the observation and the superimposed image ILR'(x) for the measurement are sequentially captured in a time division manner Thus, there might be movement between the imaging system and the object during a time interval between the timings at which the images are captured. In such a case, the amount of the movement needs to be taken into consideration to obtain the phase difference.

Figure 7:
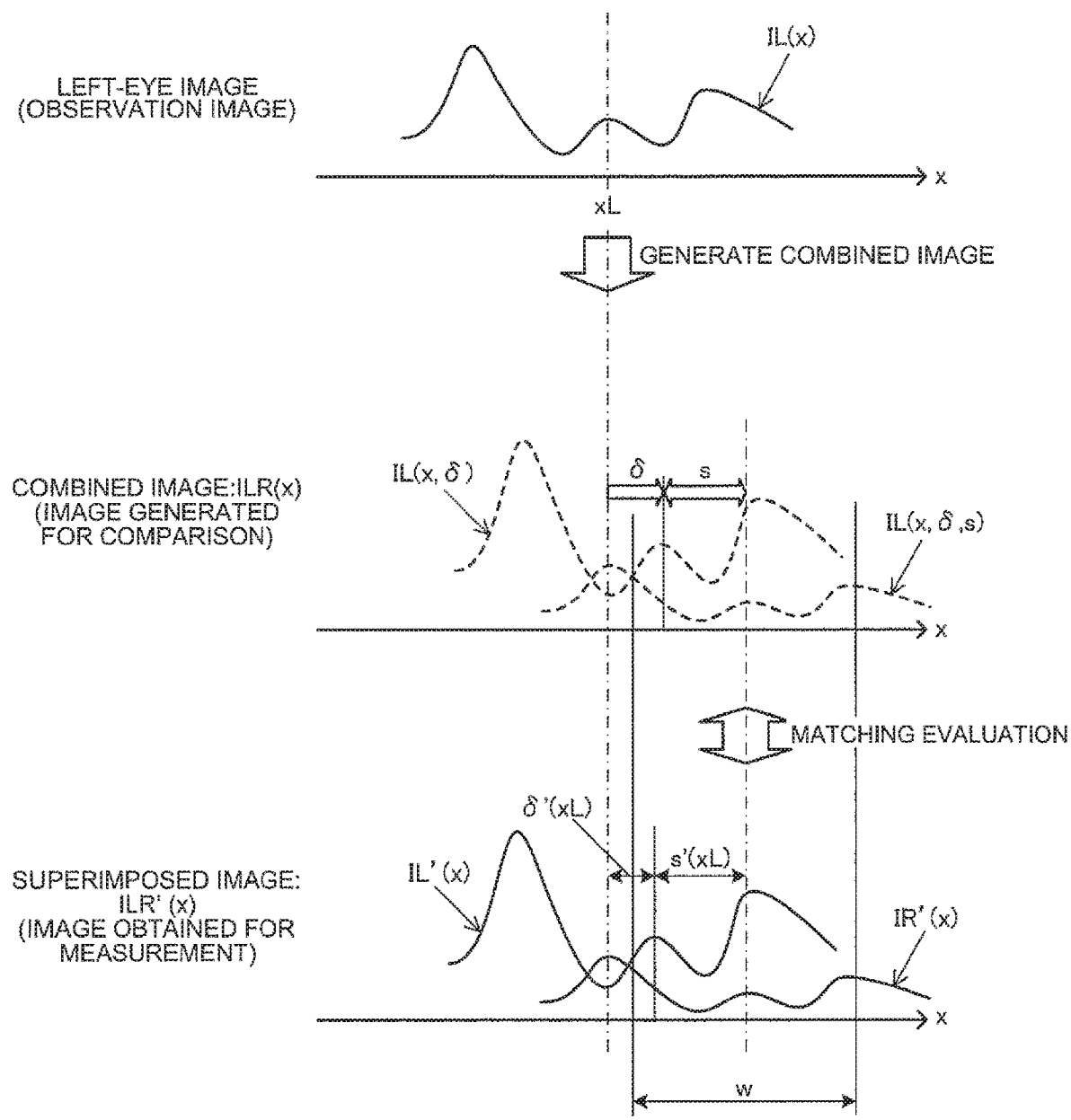
FIG. 7 illustrates phase difference detection method taking a motion into consideration.

FIG. 7 illustrates a method of detecting the phase difference while taking the movement into consideration. The simple description is given by focusing only on the x coordinate and ignoring the y coordinate. In the stereoscopic measurement mode, ILR'(x)=[IL'+IR'(x)] is obtained as the captured image. In FIG. 7, IL'(x) and IR'(x) are each illustrated as an individual waveform.

The amount δ represents the motion amount δ between the left pupil image IL(x) and the superimposed image ILR'(x) sequentially obtained. The left pupil image IL(x) for the observation is separated into the image IL(x,δ) shifted from the coordinate xL by the motion amount δ and the image IL(x,δ,s) shifted from the coordinate xL by the sum of the motion amount δ and the phase difference s. After these images are thus generated, the gain adjustment is executed as in the following Formula (3) based on IL(x) by using the ratio between the areas φL and φR of the stop holes 21 and 22.

$$\left.\begin{array}{l}IL(x,\delta)=IL(x-\delta)\\ IL(x,\delta,s)=(\phi R/\phi L)\cdot IL(x-\delta-s)\end{array}\right\} \quad (3)$$

The images as a result of the gain adjustment are referred to as IL(x,δ) and IL(x,δ,s). In Formula (3) described above, the area ratio between the stop holes 21 and 22 is used for the gain setting. However, this should not be construed in a limiting sense. For example, the optimum gain adjustment may be implemented by using the actual imaging system.

Then, IL(x,δ) and IL(x,δ,s) are combined to intentionally generate the combined image ILR(x,δ,s) as in Formula (4) described later to be used as the comparison image for the search.

$$ILR(x,\delta,s)=IL(x,\delta)+IL(x,\delta,s)=IL(x-\delta)+(\phi R/\phi L)\cdot IL(x-\delta-s) \quad (4)$$

Next, the matching evaluation is performed between the superimposed image ILR'(x) for measurement and the combined image ILR(x,δ,s) based on the phase difference s and the motion amount δ that are individually changed. Then, the phase difference s and the motion amount δ providing the highest level of matching are detected to be the phase difference s'(xL) and the motion amount δ'(xL) of the left pupil image IL'(x) and the right pupil image IR'(x) at each coordinate xL. In FIG. 7, w represents the range in which the comparison to check the similarity is performed in the matching evaluation.

This method is also performed under an assumption that the images IL(x), IL'(x), and IR'(x) are locally substantially the same. However, the image IL(x), IL'(x), and IR'(x) are images with parallax, and thus are actually different waveforms. Still, when the shifting amount s and the motion amount δ are relatively small, the local ranges of the images can be regarded as being in similar relationship.

With this method, the phase difference between the left pupil image IL'(x) and the right pupil image IR'(x) in the measurement stereoscopic image obtained by superimposing involving the motion amount δ can be detected without being affected by the motion amount δ. This is because the left pupil image IL'(x) and the right pupil image IR'(x) are simultaneously captured (as the superimposed image) under the stereoscopic measurement mode, and thus the phase difference s is unaffected by the movement. All things considered, the phase difference s can be extracted with the motion amount δ separated from the shifting amount (that is, s+δ) between the images IL(x) and ILR'(x).

6. Principle of Stereoscopic Three-Dimensional Measurement

The principle of the stereoscopic measurement in the configuration example illustrated FIG. 1 to FIG. 4 is described.

Figure 8:
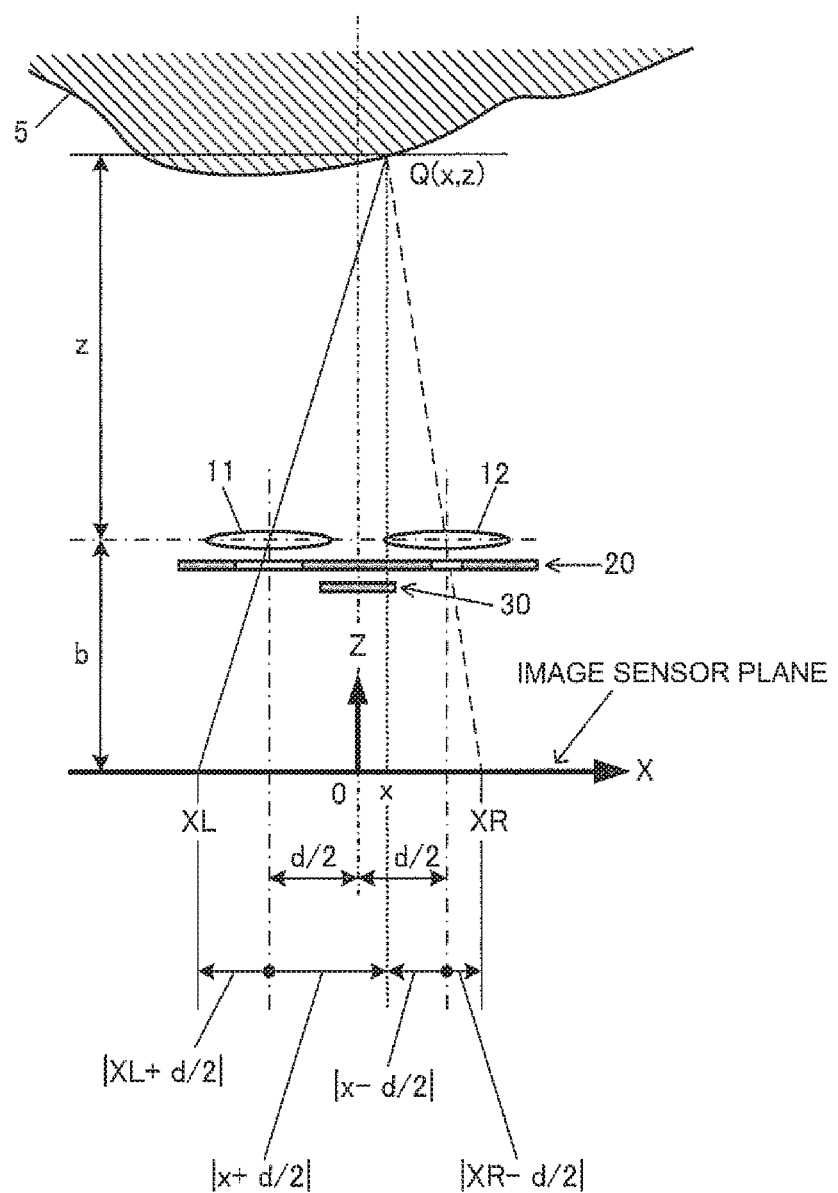
FIG. 8 illustrates a principle of stereoscopic three dimensional measurement.

As illustrated in FIG. 8, the optical paths for the left eye and the right eye are each independently formed. Reflected light from the object 5 passes through these optical paths so that the object image is formed on the image sensor plane (light receiving surface). A coordinate system X, Y, Z in the three-dimensional space is defined as follows. Specifically, an X axis and a Y axis orthogonal to the X axis are set along the image sensor plane. A Z axis, toward the object, is set to be in a direction that is orthogonal to the image sensor plane, and parallel to the optical axes AX1 and AX2. The Z axis, the X axis, and the Y axis intersect at the zero point. The Y axis is omitted for the sake of illustration.

Here, the distance between the imaging optical system 11, 12 (imaging lens) and the image sensor plane is defined as b, and the distance between the imaging optical system 11, 12 and a certain point Q(x,z) of the object 5 is defined as z. The optical axes AX1 and AX2 are arranged to be at the same distance from the Z axis. This distance is defined as d/2. Thus, the baseline length for the stereoscopic measurement is d. An X coordinate of a corresponding point, corresponding to the certain point Q(x,y) of the object 5, as a part of an image formed on the image sensor plane with the imaging optical system 11 is XL. An X coordinate of the corresponding point, corresponding to the certain point Q(x,y) of the object 5, as a part of the image formed on the image sensor plane with the imaging optical system 12 is XR. The following Formula (5) can be obtained based on a similarity relation among a plurality of partial right angle triangles formed within a triangle defined by the certain point Q(x,z) and the coordinates XL and XR.

$$\frac{z}{b} = \frac{|x+d/2|}{|XL+d/2|} = \frac{|x-d/2|}{|XR-d/2|} \quad (5)$$

The following Formulae (6) and (7) hold true.

$$\left.\begin{array}{l} x+d/2 > 0 \text{ when } XL+d/2 < 0 \\ x+d/2 < 0 \text{ when } XL+d/2 > 0 \end{array}\right\} \quad (6)$$

$$\left.\begin{array}{l} x-d/2 > 0 \text{ when } XR-d/2 < 0 \\ x-d/2 < 0 \text{ when } XR-d/2 > 0 \end{array}\right\} \quad (7)$$

Thus, the absolute value in Formula (5) described above can be normal values as in the following Formula (8).

$$\frac{z}{b} = -\frac{x+d/2}{XL+d/2} = -\frac{x-d/2}{XR-d/2} \quad (8)$$

Formula (8) described above can be solved for x as in the Formula (9).

$$x = -\frac{d}{2} \cdot \frac{XR+XL}{XR-XL-d} \quad (9)$$

The following Formula (10) for obtaining z can be obtained by substituting x in Formula (9) described above into Formula (8) described above.

$$z = \frac{d}{(XR-XL-d)} \cdot b \quad (10)$$

Note that d and b are known setting values, and an unknown value (XR−XL) is detected as the phase difference s through the matching processing (correlation calculation) described above. The object shape can be measured by calculating the distance z for each position x. Some distances z might be unobtainable due to matching failure. Such distances z may be obtained by interpolation using the distances z obtained for the surrounding pixels or by other like method, for example.

7. Detailed Configuration of Endoscope Apparatus

Figure 9:
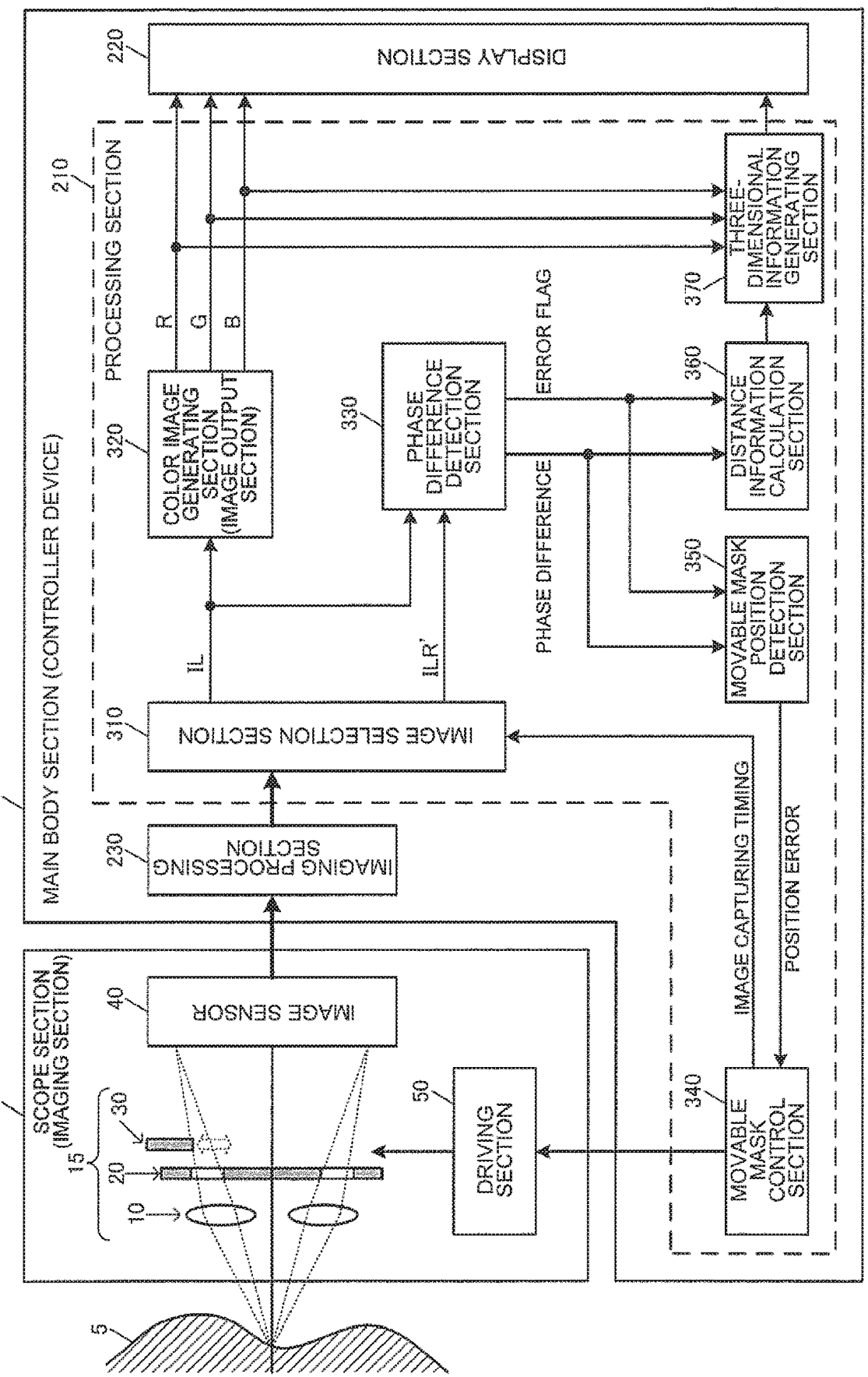
FIG. 9 illustrates a detailed configuration example the endoscope apparatus.

FIG. 9 illustrates a detailed configuration example of an endoscope apparatus (an imaging device in a broad sense). The endoscope apparatus includes a scope section 100 (imaging section) and a main body section 200 (controller device). The scope section 100 includes the optical system 15, the image sensor 40, and the driving section 50. The optical system 15 includes the imaging optical system 10, the fixed mask 20, and the movable mask 30. The main body section 200 includes a processing section 210 (processing circuit, processing device), a display section 220 (display device), and the imaging processing section 230 (imaging processing circuit). The processing section 210 includes the image selection section 310 (image frame selection unit), the color image generating section 320 (image output section), the phase difference detection section 330, the movable mask control section 340 (mode control section), the movable mask position detection section 350, the distance information calculation section 360, and the three-dimensional information generating section 370.

The scope section 100, the color image generating section 320, the movable mask control section 340, and the movable mask position detection section 350 respectively correspond to the imaging section 105, the image output section 325, the mode control section 345, and the error detection section 355 in FIG. 5. The storage section 410 and the operation section 420 in FIG. 5 are omitted in FIG. 9. The scope section 100 may further include unillustrated components such as a treatment instrument and an illumination device (such as a light source and a lens).

The endoscope apparatus may be what is known as a video scope (an endoscope apparatus incorporating an image sensor) for industrial and medical use. The present invention can be applied to a flexible endoscope with the scope section 100 that is flexible and to a rigid endoscope with the scope section 100 that is in a form of a stick. For example, a flexible endoscope for industrial use includes the main body section 200 and the scope section 100 serving as a portable device that can be carried around. The flexible endoscope is used for inspection in manufacturing and maintenance processes for industrial products, in a maintenance process for buildings and pipes, and in other like situations.

The driving section 50 drives the movable mask 30 based on the control signal from the movable mask control section 340, to switch between the first state (observation mode) and the second state (stereoscopic measurement mode). For example, the driving section 50 includes an actuator including a piezoelectric element and a magnet mechanism.

The imaging processing section 230 executes an imaging process on a signal from the image sensor 40, and outputs a captured image (such as a Bayer image, for example). For example, a correlative double sampling process, a gain control process, an A/D conversion process, gamma correction, color correction, noise reduction, and the like are executed. For example, the imaging processing section 230 may include a discrete IC such as an ASIC, or may be incorporated in the image sensor 40 (sensor chip) and the processing section 210.

The display section 220 displays an image captured by the scope section 100, three-dimensional shape information on the object 5, or the like. For example, the display section 220 includes a liquid crystal display, an Electro-Luminescence (EL) display, and the like.

An operation of the endoscope apparatus is described below. The movable mask control section 340 controls the driving section 50, and thus switches the position of the movable mask 30. When the movable mask control section 340 sets the movable mask 30 to be in the observation mode, an image of the object 5 is formed on the image sensor 40 with reflected light from the object 5 that has passed through the left-eye optical path. The imaging processing section 230 reads out pixel values of the image formed on the image sensor 40, performs the A/D conversion or the like, and outputs resultant image data to the image selection section 310.

The image selection section 310 detects that the movable mask 30 is in the state corresponding to the observation mode based on the control signal from the movable mask control section 340, and outputs the captured image IL(x) to the color image generating section 320 and the phase difference detection section 330. The color image generating section 320 performs demosaicing process (process for generating an RGB image from a Bayer image) and various image processes, and outputs the resultant RGB primary color image to the display section 220. The display section 220 displays this color image.

When the movable mask control section 340 sets the movable mask 30 to be in the stereoscopic measurement mode, images are simultaneously formed on the image sensor 40 based on the reflected light from the object 5, through the left-pupil optical path and the right-pupil optical path. The imaging processing section 230 reads out pixel values of the image formed on the image sensor 40, performs the A/D conversion or the like, and outputs resultant image data to the image selection section 310.

The image selection section 310 detects that the movable mask 30 is in the state corresponding to the stereoscopic measurement mode based on the control signal from the movable mask control section 340, and outputs the captured image ILR'(x) to the phase difference detection section 330. The phase difference detection section 330 convers the image IL(x) and the image ILR'(x) into monochrome images, executes matching processing described above on the images thus obtained by the conversion, and detects the phase difference (phase shift) for each pixel. The phase difference detection section 330 determines whether the detected phase difference is reliable, and outputs an error flag for each pixel determined to have an unreliable phase difference. Various matching evaluation methods for obtaining the phase difference between two similar waveforms (the image ILR(x) and the image ILR'(x)) have conventionally been proposed, and thus can be used as appropriate. The proposed methods include normalized correlation calculation such as Zero-mean Normalized Cross-Correlation (ZNCC), and Sum of Absolute Difference (SAD) based on the sum of absolute differences between the waveforms.

The images do not necessarily need to be converted into monochrome images. The phase difference may be detected by using red components R, green components G, blue components B, and infrared components in the left pupil image IL(x) and the superimposed image ILR'(x). When the object has unbalanced color components, the color component corresponding to the highest imaging sensitivity and the highest SN ratio can be effectively used for the detection.

When the image sensor 40 has sensitivity covering the near infrared wavelength band, the object 5 may be selectively irradiated with visible light or infrared light. Then, a visible image or a near infrared image can be selectively obtained as the observation image IL(x) and the superimposed image ILR'(x) for measurement obtained with two pupils. The visible image may be obtained to pursue color purity. The visible image and the near infrared image may be simultaneously obtained to pursue the high sensitivity and the high SN ratio. Only the near infrared image may be obtained for special purposes.

The phase difference detection section 330 outputs the phase difference information thus detected, and the error flag to the distance information calculation section 360. The distance information calculation section 360 calculates the distance information (for example, the distance z in FIG. 8) on the object 5 for each pixel, and outputs the resultant distance information to the three-dimensional information generating section 370. For example, the pixel provided with the error flag may be regarded as a flat portion of the object 5 (an area with a small amount of edge components), and interpolation may be performed for such pixel based on the distance information on surrounding pixels. The three-dimensional information generating section 370 generates three-dimensional information from the distance information (or from the distance information and the RGB image from the color image generating section 320). The three-dimensional information may be various types of information including a Z value map (distance map), polygon, and a simulative-three-dimensional display image (with shape emphasized by shading or the like, for example). The three-dimensional information generating section 370 generates a three-dimensional image and three-dimensional data generated, or a display image obtained by superimposing the observation image on the image as appropriate, and outputs the resultant image and/or data to the display section 220. The display section 220 displays the three-dimensional information.

The movable mask position detection section 350 detects whether the movable mask 30 is at the position corresponding to the observation mode or at the position corresponding to the stereoscopic measurement mode by using the images IL(x) and ILR'(x) used in the stereoscopic measurement mode. When the movable mask 30 is in the state not matching the mode, a position error flag is output to the movable mask control section 340. Upon receiving the position error flag, the movable mask control section 340 corrects the movable mask 30 to be in the correct state (state corresponding to the image selection). When the correction operation cannot achieve the correct state, some sort of failure is determined to have occurred, and thus the function of the entire system is stopped.

For example, whether the movable mask 30 is at the position corresponding to the observation mode or is at the position corresponding to the stereoscopic measurement mode determined through the following methods 1 to 4. One or a plurality of the first to the fourth methods may be employed.

In the first method, whether or not an average value of the phase differences s within a predetermined region of the image is of a negative value is determined. This method is for a case where the movable mask 30 erroneously closes the left-eye optical path under the observation mode. In such a case, the right pupil image IR(x) is obtained as the reference image, which is supposed to be the left pupil image IL(x), leading to reversed positional relationship between the images IL'(x) and IR'(x) forming the superimposed image ILR'(x), resulting in the phase difference s of a negative value.

In the second method, whether or not the matching evaluation value for detecting the phase difference s is equal to or lower than a predetermined value is determined. This method is for a case where the left-or the right-eye optical path is incompletely closed under the observation mode. In such a case, matching is evaluated between double images with different profiles. Such evaluation results in a low matching evaluation value obtained with the phase difference s that is supposed to indicate the match.

In the third method, whether or not the average value of the phase differences s within a predetermined region of the image is equal to or smaller than a predetermined value (a value close to 0) is determined. This method is for a case where the left- or the right-eye optical path is closed under the stereoscopic measurement mode. In such a case, an image with no phase difference s over the entire imaging area is obtained. Thus, the phase difference s is substantially 0.

In the fourth method, whether or not a brightness ratio between the observation image IL(x) and the superimposed image ILR'(x) for measurement is within a predetermined range is determined. When the movable mask 30 is properly operating, a substantially constant brightness ratio between the images is achieved.

8. Mode Switching Sequence

Figure 10:
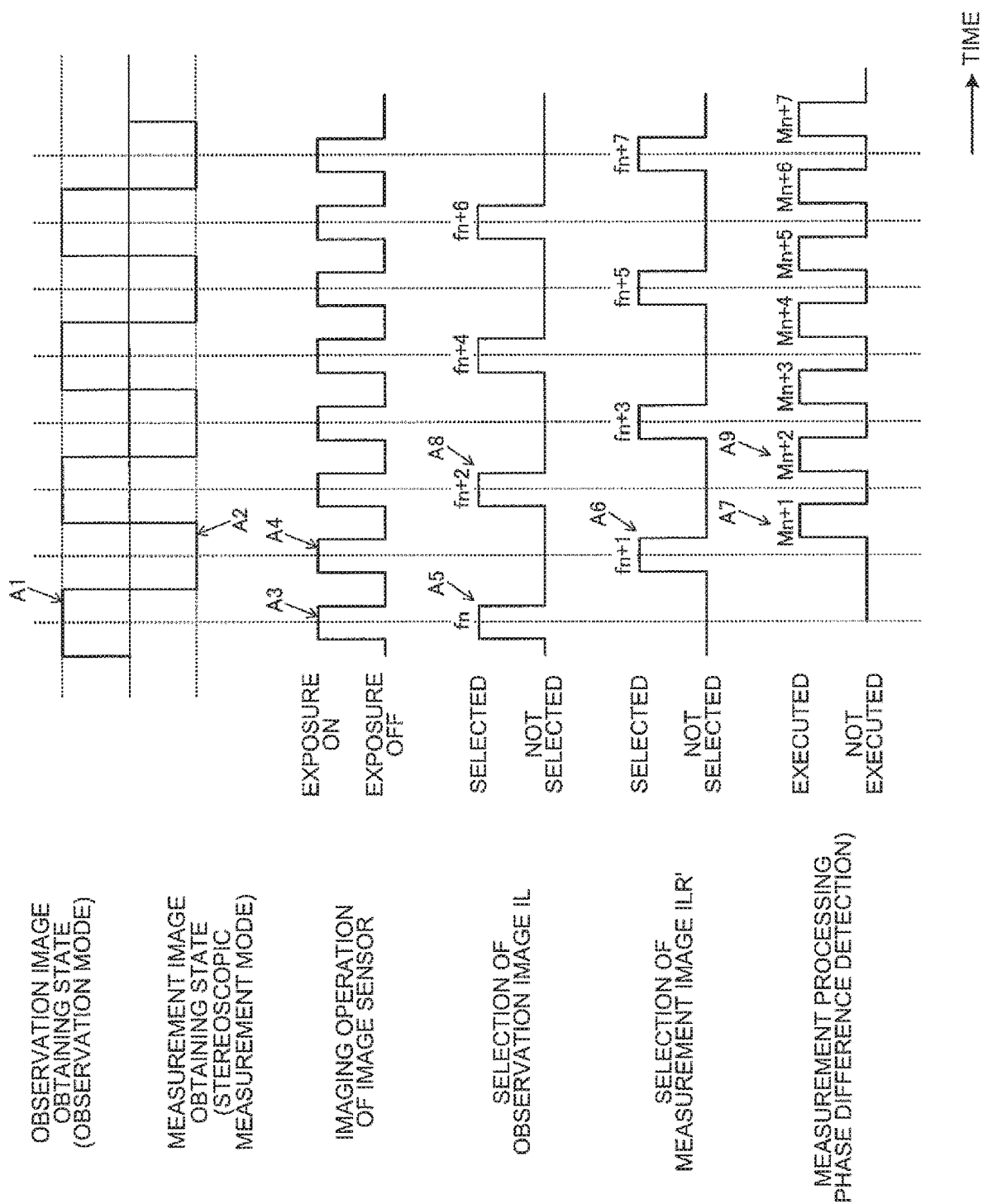
FIG. 10 illustrates a first sequence of operations in movie capturing.

FIG. 10 illustrates a first sequence (first timing chart) of a movie capturing operation.

As illustrated in FIG. 10, switching of the state of the movable mask 30, an image capturing timing, and selection of the captured image are interlocked. As indicated by A1 and A2, the mask state corresponding to the observation mode and the mask state corresponding to the stereoscopic measurement mode are alternately achieved. As indicated by A3 and A4, an image is captured each time the mask state changes. As indicated by A5, the image captured with the image sensor 40 in a frame fn with the mask state corresponding to the observation mode is selected as an observation image IL(x). As indicated by A6, the image captured with the image sensor 40 in a frame fn+1 with the mask state corresponding to the stereoscopic measurement mode is selected as the measurement image ILR'(x).

With the observation mode and the stereoscopic measurement mode thus alternately repeated, the observation image IL(x) and the measurement image ILR'(x) can be contiguously obtained substantially in real time. Thus, the monitoring and the measurement can both be achieved even when the object 5 moves. When the observation image IL(x) is displayed with measurement information overlaid as appropriate, useful information can be provided so that the user can perform visual inspection and quantitative inspection at the same time.

The measurement processing is executed by using the observation image IL(x) and the measurement image ILR'(x) subsequently obtained, or by using the measurement image ILR'(x) and the observation image IL(x) subsequently obtained. For example, as indicated by A7, measurement processing Mn+1 is executed with the observation image IL(x) captured in the frame fn and the measurement image ILR'(x) captured in the frame fn+1, in a measurement period after an image capturing period in the frame fn+1. Alternatively, as indicated by A8, the observation image IL(x) is captured in a frame fn+2, and as indicated by A9, measurement processing Mn+2 is executed with the measurement image ILR'(x) captured in the frame fn+1 and the observation image IL(x) captured in fn+2, in a measurement period after the image capturing period in the frame fn+2. Thus, measurement information can be obtained substantially in real time in each frame.

FIG. 11 illustrates a second sequence (second timing chart) of operations in a movie capturing.

In FIG. 11, a mask state for the observation mode is set in a single frame as indicated by B1, and a mask state for the stereoscopic measurement mode is set in a plurality of subsequent frames as indicated by B2. FIG. 11 illustrates an example where the plurality of frames are five frames. However, this should not be construed in a limiting sense. A single image is captured with the mask state for the observation mode as indicated by B3, and the image thus captured in the frame fn is selected as the observation image IL(x) as indicated by B4. Five images are captured with the mask state for the stereoscopic measurement mode as indicated by B5, and these images captured in frames fn+1 to fn+5 are each selected as the measurement image ILR'(x) as indicated by B6.

The frames fn+1 to fn+5 are referred to as fn+i (i is an integer satisfying 1≤i≤5). In the measurement period after the image capturing period in the frame fn+i, the measurement processing Mn+i is executed with the observation image IL(x) captured in the frame fn and the measurement image ILR'(x) captured in the frame fn+i. Then, the phase difference s'(xL) is obtained through the following Formula (11). In the formula, s'(xL)i represents a phase difference at a certain pixel (coordinate) xL on the image sensor 40 in the frame fn+i, j is the number of measurement images ILR'(x) captured for the single observation image IL(x). In FIG. 11, j is five.

$$s'(xL) = \frac{1}{j}\sum_{i=1}^{j} s'(xL)i \qquad (11)$$

With a phase differences s'(xL)n thus obtained integrated and averaged within the frames (fn+1 to fn+5), a more accurate phase difference s'(xL) with can be obtained with small fluctuation. The phase difference s'(xL)n is preferably obtained with the influence of the movement between frames eliminated (using the method illustrated in FIG. 7).

9. Second Configuration Example

Figure 12:
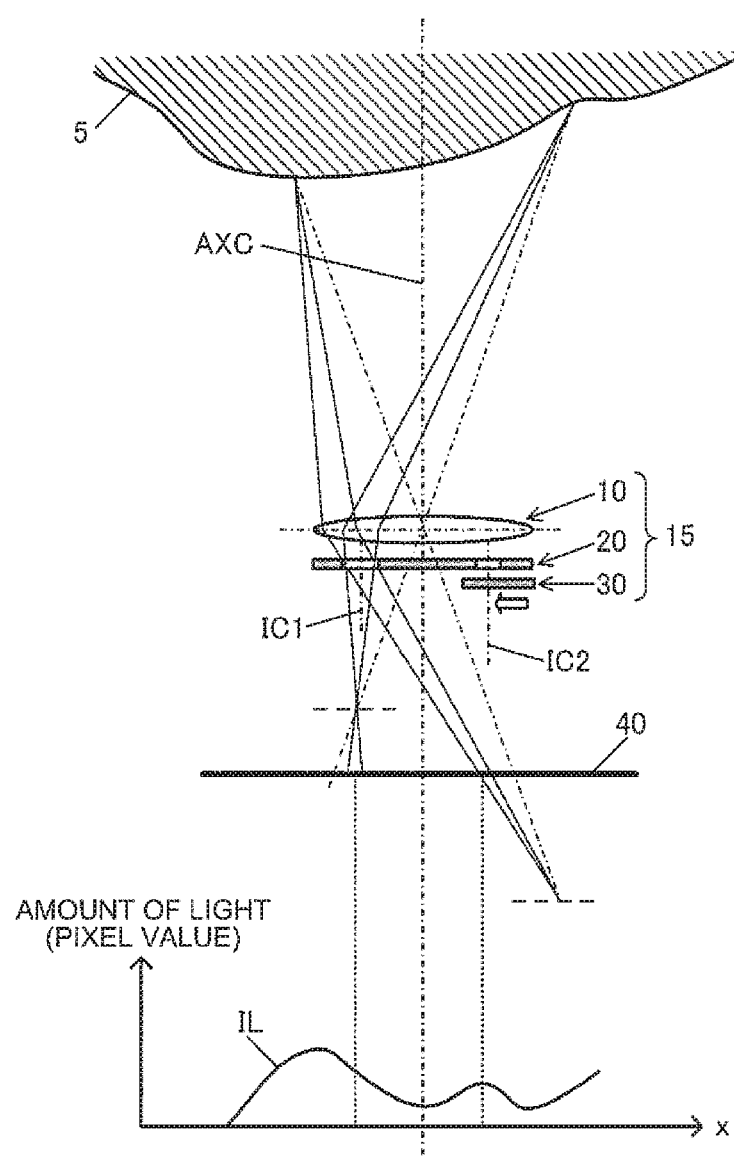
FIG. 12 illustrates a second configuration example of the imaging section of the endoscope apparatus.
Figure 13:
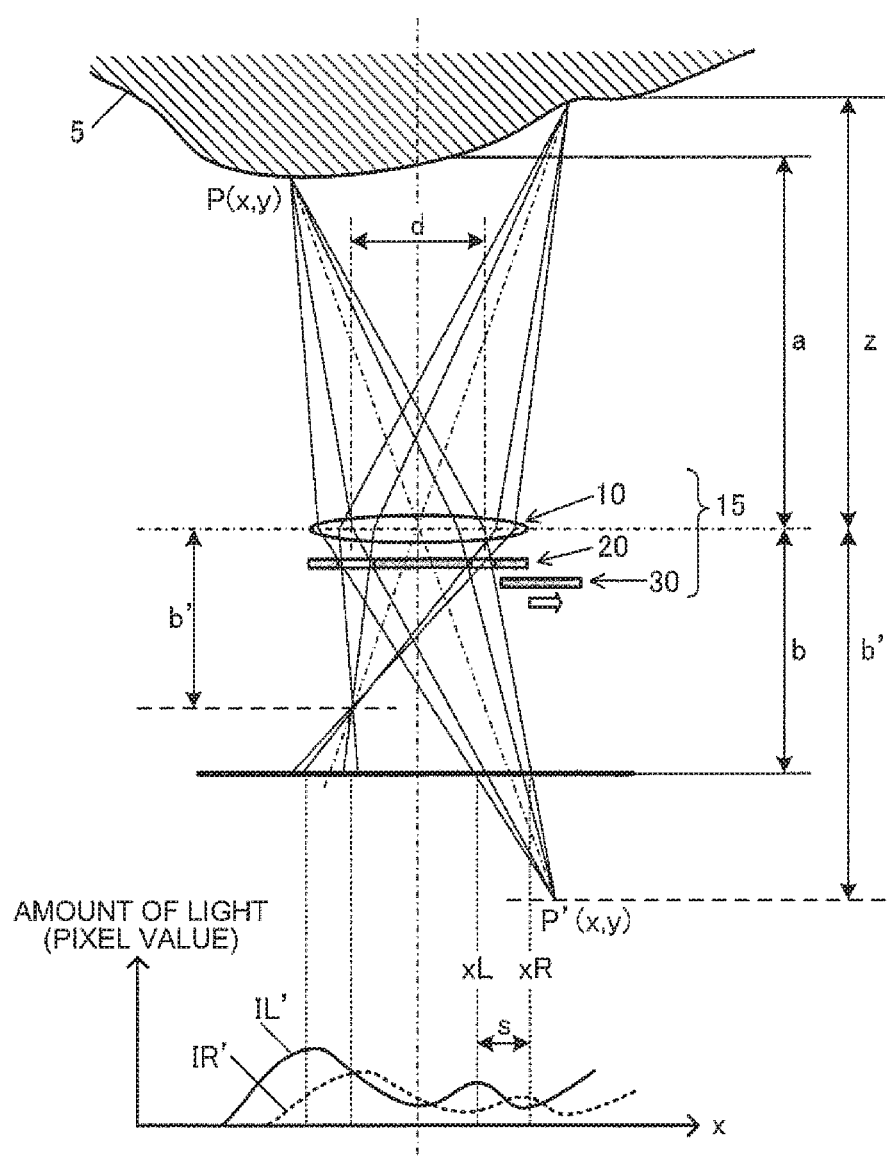
FIG. 13 illustrates the second configuration example of the imaging section of the endoscope apparatus.
Figure 14:
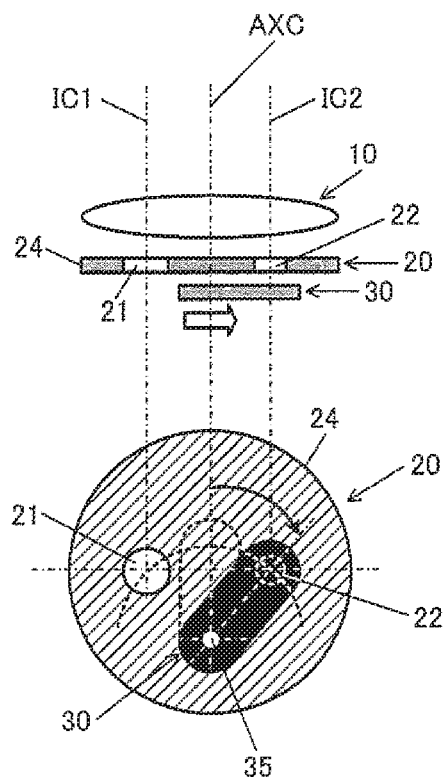
FIG. 14 illustrates a second detail configuration example of the fixed mask and the movable mask.
Figure 15:
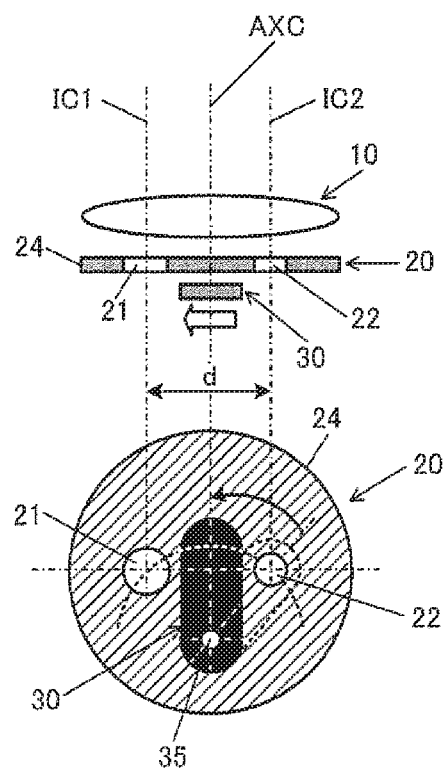
FIG. 15 illustrates the second detail configuration example of the fixed mask and the movable mask.

FIG. 12 and FIG. 13 illustrate a second basic configuration example of an imaging section of an endoscope apparatus. FIG. 14 and FIG. 15 illustrate a second detailed configuration example of the fixed mask 20 and the movable mask 30. FIG. 12 and FIG. 13 are each a cross-sectional side view of the imaging section (as viewed along a plane including an optical axis) and illustrate relationship between an amount of light of an image formed on the image sensor (or a pixel value of the image captured with the image sensor) and the position x. FIG. 14 and FIG. 15 each include a cross-sectional view of the imaging optical system 10, the fixed mask 20, and the movable mask 30, and a diagram illustrating the fixed mask 20 and the movable mask 30 as viewed in the optical axis direction (a back view as viewed from the image side). The components that are the same as those described above with reference to FIG. 1 to FIG. 4 are denoted with the same reference signs, and the description thereof is omitted as appropriate.

As illustrated in FIG. 12 to FIG. 15, the imaging optical system 10 may include a monocular optical system. The monocular optical system includes one or a plurality of lenses. The monocular optical system has a single pupil divided into a left pupil and a right pupil with the stop holes 21 and 22 of the fixed mask 20. Center lines IC1 and IC2 are defined as lines that pass through the centers of the stop holes 21 and 22 (the center of a circle when the stop hole has a circular shape for example) and are in parallel with an optical axis AXC of the imaging optical system 10. For example, the center lines IC1 and IC2 are arranged to be at an equal distance from the optical axis AXC. For example, the fixed mask 20 is provided at a pupil position of the imaging optical system 10. The movable mask 30 is set to be at a position to shield the stop hole 22 from light in the observation mode illustrated in FIG. 12 and FIG. 14. The movable mask 30 is set to be at a position to open the stop holes 21 and 22 in the stereoscopic measurement mode illustrated in FIG. 13 and FIG. 15.

In this configuration example, the area φL of the stop hole 21 is different from the area φR of the stop hole 22. For example, the stop hole 22 is smaller than the stop hole 21. In FIG. 12 to FIG. 15, φL>φR holds true. However, this should not be construed in a limiting sense, and a configuration satisfying φL<φR may be employed.

In the monocular optical system, the phase difference s is 0 at a position where the object is in focus, and becomes a positive or negative value (the right pupil image IR' is shifted from the left pupil image IL' on one of opposite sides) with the focal point shifted forward or rearward. In the present embodiment, the left pupil image IL' and the right pupil image IR' have different brightness values, so that the side on which the right pupil image IR' is shifted from the left pupil image IL' can be determined from the superimposed image.

In the stereoscopic optical system illustrated in FIG. 1 to FIG. 4, the phase difference s remains to be a positive or negative value (the right pupil image IR' is shifted from the left pupil image IL' toward the same side) regardless of the focus status. Thus, the left pupil image IL' and the right pupil image IR' do not need to have different values of brightness.

This configuration example employs a method that is the same as that described above with reference to FIG. 6 or FIG. 7 to detect a phase difference s(x) from the image IL(x) captured in the observation mode and the image ILR'(x) captured in the stereoscopic measurement mode. Similarly, the endoscope apparatus according to this configuration example may have a configuration similar to that illustrated in FIG. 5 and FIG. 9.

10. Third Configuration Example

FIG. 16 and FIG. 17 illustrate a third detailed configuration example of the fixed mask 20 and the movable mask 30. FIG. 16 and FIG. 17 each include a cross-sectional view of the imaging optical system 10, the fixed mask 20, and the movable mask 30, and a diagram illustrating the fixed mask 20 and the movable mask 30 as viewed in the optical axis direction (a back view as viewed from the image side). The components that are the same as those described above with reference to FIG. 1 to FIG. 4 and FIG. 12 to FIG. 15 are denoted with the same reference signs, and the description thereof is omitted as appropriate.

As illustrated in FIG. 16 and FIG. 17, the imaging optical system 10 may include a single optical system. The fixed mask 20 has the light shielding section 24 provided with a single stop hole 23 (through hole). In the observation mode illustrated in FIG. 16, the movable mask 30 is set to be at the position for opening the stop hole 23. In the stereoscopic measurement mode illustrated in FIG. 17, the movable mask 30 is set to be at a position for dividing the stop hole 23 into two holes (referred to as FL and FR). With these holes FL and FR, a single pupil of the monocular optical system is divided into the left pupil and the right pupil.

For example, the stop hole 23 has a circular shape and has the center line (the center of the circle) matching the optical axis AXC. The movable mask 30 has the light shielding section with a width (width in a direction orthogonal to the longitudinal direction) smaller than the size (diameter) of the stop hole 23. In the stereoscopic measurement mode, the movable mask 30 is configured in such a manner that the holes FL and FR have different areas φL and φR. For example, the rotational shaft 35 may be arranged in an eccentric manner so that the center line of the light shielding section of the movable mask 30 in the longitudinal direction does not pass through the center of the stop hole 23 when the rotational angle is 0.

With this configuration example, the stop hole 23 with a large opening can be used, whereby the bright observation image IL(x) can be captured. The stop hole 23 has the center line matching the optical axis AXC so that a high quality image (with features such as small distortion and a large angle of view) can be captured by using the light passing through the center of the optical axis of the imaging optical system 10.

This configuration example employs a method that is the same as that described above with reference to FIG. 6 or FIG. 7 to detect the phase difference s(x) from the image IL(x) captured in the observation mode and the image ILR'(x) captured in the stereoscopic measurement mode. Similarly, the endoscope apparatus according to this configuration example may have a configuration similar to that illustrated in FIG. 5 and FIG. 9.

11. Principle of Stereoscopic Three-Dimensional Measurement

The principle of the stereoscopic three-dimensional measurement in the second configuration example illustrated in FIG. 12 to FIG. 15 and the third configuration example illustrated FIG. 16 and FIG. 17 is described.

As illustrated in FIG. 13, an X axis and a Y axis orthogonal to the X axis are set along the image sensor plane. A Z axis, toward the object, is set to be in a direction that is orthogonal to the image sensor plane, and parallel to the optical axis AXC. The Z axis, the X axis, and the Y axis intersect at the zero point. The Y axis is omitted for the sake of illustration.

An appropriate distance between the imaging optical system 10 (imaging lens) and a measurement point of the object is defined as z, and a distance between an end of z and the focal point is defined as b'. A distance between the imaging optical system 10 and a reference measurement point is defined as a, and a distance between the imaging optical system 10 and an image sensor plane is defined as b. The reference measurement point is a point with which the focal point on the image sensor plane is achieved. The left and the right pupils (the centers of gravities of the pupils) are separated from each other by a distance d. An X coordinate of the center of gravity of an image of a certain point P(x,y) of the object formed with the left pupil on the image sensor plane is defined as xL, and an X coordinate of the center of gravity of an image of the point P(x,y) of the object formed with the right pupil on the image sensor plane is defined as xR. The following formulae can be obtained based on similar relationship among a plurality of triangular sections formed in a triangle defined by lines connecting a certain point P(x,z), a focal point P'(x,z), and the coordinates xL,xR.

The following Formula (12) represents the phase difference s corresponding to the shifting amount between the left pupil image and the right pupil image. The value s is a positive value, a negative value, or 0.

$$s = xR - xL \tag{12}$$

The following Formula (13) can be obtained based on the similar relationship between triangles.

$$\frac{s}{d} = \frac{b - b'}{b'} \tag{13}$$

The following Formulae (14) and (15) are obtained based on the principle of focus relationship, with f representing the focal distance of the imaging optical system 10.

$$\frac{1}{a} + \frac{1}{b} = \frac{1}{f} \tag{14}$$

$$\frac{1}{z} + \frac{1}{b'} = \frac{1}{f} \tag{15}$$

The following Formula (16) can be obtained by removing b' and f from Formulae (13) to (15).

$$z = \frac{(ab) \cdot d}{b \cdot d - a \cdot s} \tag{16}$$

Because a, b, and d are known setting values, the distance z to the object can be obtained if the phase difference s can be obtained. The shape of the object can be measured by detecting the position xR corresponding a position xL on the image sensor plane based on the phase difference s by matching processing (correlation calculation), and calculating the distance z for all of the positions xL. Note that the distance z may not be obtainable at a position where favorable matching is unobtainable.

12. Reason why Stop Holes have Different Areas

In the second configuration example illustrated in FIG. 12 to FIG. 15 and in the third configuration example illustrated in FIG. 16 and FIG. 17, the opening areas φL and φR of the stop holes 21 and 22 (or FL and FR) of the left and the right pupil paths are intentionally set to be different from each other.

The reason why such a configuration is employed is described below using the distances z, b', a, and b, and the positions xL and xR illustrated in FIG. 13. The direction in which the right pupil image is shifted from the left pupil image on the image sensor plane is opposite between cases where the distance between the imaging optical system 10 (imaging lens) and the measurement point is shorter than the reference distance a and in a case where the distance is longer than the reference distance a. Specifically, the relationship expressed in the following Formula (17) is satisfied, so that a larger one of z and a changes from one to the other based on the shifted direction.

$$\left. \begin{array}{l} xL < xR(xR - xL > 0) \text{ when } z < a \\ xL = xR \text{ when } z = a \\ xL > xR(xR - xL < 0) \text{ when } z > a \end{array} \right\} \tag{17}$$

Thus, when the left pupil image IL'(x) and the right pupil image 'IR(x) can be regarded as substantially the same, an image obtained by superimposing these images with the same brightness does not enable the observer to recognize which one of the superimposed images has shifted in which one of left and right directions.

In view of this, in the present embodiment, the areas φL and φR of the stop holes 21 and 22 (or FL and FR) of the left and the right pupil paths are intentionally set to be different from each other. If the left pupil image IL'(x) and the right pupil image IR'(x) have different values of brightness, the superimposed image ILR'(x) varies depending on which one of the left and right direction the right pupil image IR'(x) has shifted relative to the left pupil image IL'(x). This enables the observer to recognize the shifted direction.

If the left pupil image IL'(x) and the right pupil image IR'(x) have different values of brightness, the superimposed image ILR'(x) is likely to be more different among superimposing manners, whereby the shifting amount can be more accurately detected.

13. Third Method for Detecting Phase Difference

In FIG. 6 and FIG. 7, the phase difference s is detected under an assumption that the area ratio (φR/φL) between the stop holes 21 and 22 is the same over the entire pixel positions. However, the component ratio between IL'(x) and IR'(x) in the superimposed image ILR'(x) might vary among pixel positions. In such a case, the area ratio (φR/φL) cannot be regarded as being the same. For example, the profile of the image ILR'(x) varies due to the change in the viewpoint relative to the object and the imaging position on the image sensor plane. In such a case, the accuracy of matching using the combined image ILR(x,δ,s) might be compromised in actual use.

In view of this, the present method includes calculating the component ratio between the image IL'(x) and the image IR'(x) each time the ratio changes, and generating the combined image with the image IL(x) and the image IR(x) with the component ratio matching that between the image IL'(x) and the image IR'(x). Thus, the matching evaluation can be accurately executed.

Figure 18:
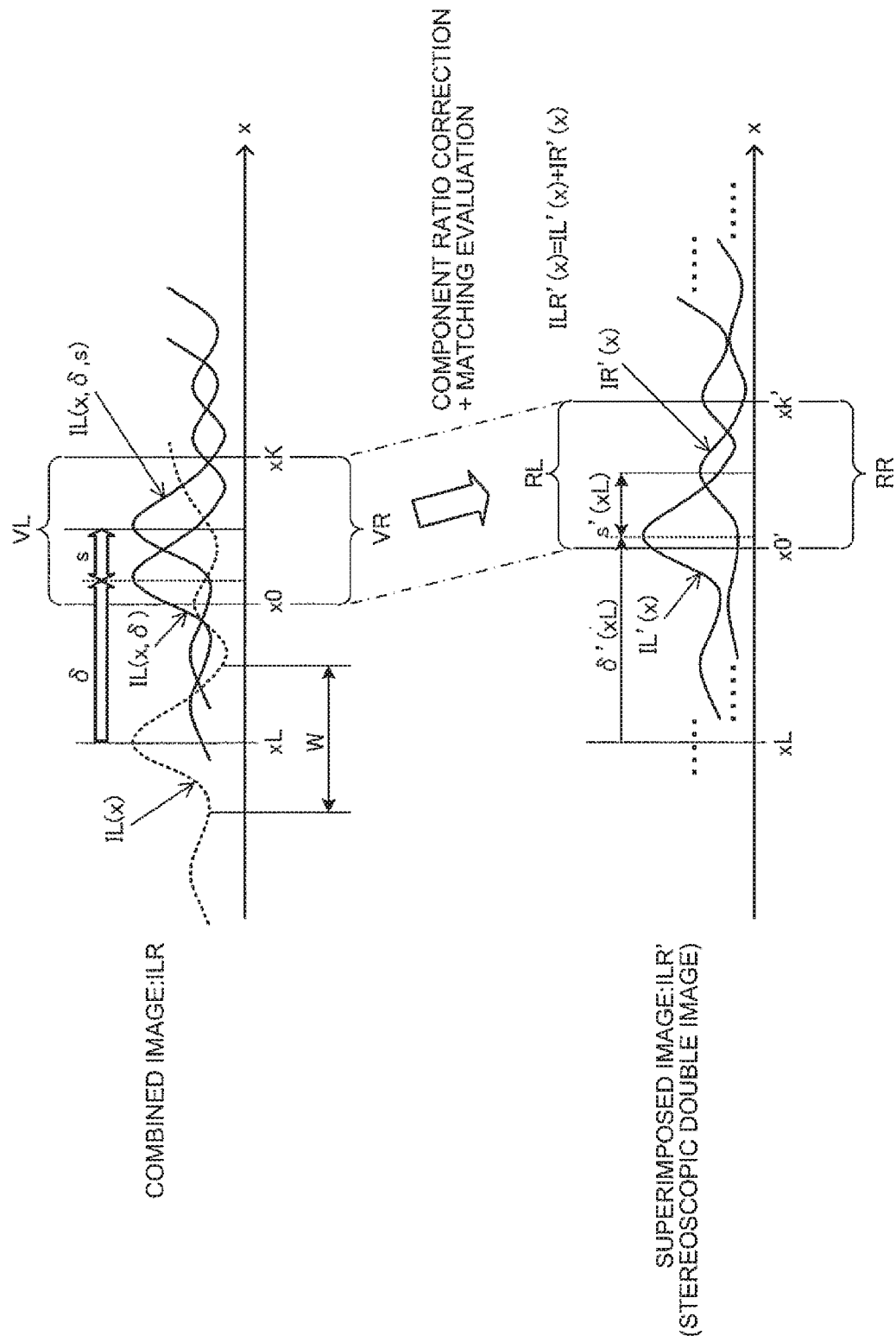
FIG. 18 illustrates a third phase difference detection method.

As illustrated in FIG. 18, vectors VL, VR, RL, and RR are each illustrated as a sampling sequence (a pixel value sequence) within a predetermined with w.

The vector VL is a sampling sequence in the image IL(x,δ). The vector VR is a sampling sequence in the image IL(x,δ,s). A composite vector CV is a sampling sequence in the image ILR(x,δ,s). These images are generated from images captured in the observation mode, and are defined by Formula (3) and (4) described above. The vector RL is a sampling sequence in the image IL'(x). The vector RR is a sampling sequence in the image IR'(x). A superimposed vector CR is a sampling sequence in the image ILR'(x). The image ILR'(x) is an image captured in the stereoscopic measurement mode and is formed by the images IL'(x) and IR'(x).

Coordinates xk, xk' of each vector component are defined as in the following Formula (18) based on a certain sampling position xL. In the figure, K represents the number of sampling times in the section w (the number of pixels in the section w in the parallax direction (x direction)).

$$xk = xL + \delta - (w/2) + k, xk' = xL + \delta' - (w/2) + k \quad (k=0,1,2,\ldots,K) \quad (18)$$

Using this Formula (18), the components of each vector can be expressed as in the following Formulae (19) and (20).

$$\begin{aligned} VL &= [IL(x0-\delta), IL(x1-\delta), IL(x2-\delta), \ldots, IL(xK-\delta)] \\ VR &= [IL(x0-\delta-s), IL(x1-\delta-s), IL(x2-\delta-s), \ldots, IL(xK-\delta-s)] \\ CV &= VL + VR \end{aligned} \quad (19)$$

$$\begin{aligned} RL &= [IL'(x0'-\delta'), IL'(x1'-\delta'), IL'(x2'-\delta'), \ldots, IL'(xK'-\delta')] \\ RR &= [IL'(x0'-\delta'-s'), IL'(x1'-\delta'-s'), IL'(x2'-\delta'-s'), \ldots, IL'(xK'-\delta'-s')] \\ CR &= RL + RR \end{aligned} \quad (20)$$

The image IL(x,δ) and the image IL'(x) can be regarded as being in similar relationship, and the image IL(x,δ,s) and the image IR'(x) can be regarded as being in similar relationship. The following Formula (21) can be obtained with gL representing a correction coefficient for the magnitude of a vector in a case where the image IL(x,δ) and the image IL'(x) match, and gR representing a correction coefficient for the magnitude of a vector in a case where the image IL(x,δ,s) and the image IR'(x) match.

$$RL = gL \cdot VL, RR = gR \cdot VR \quad (21)$$

With the correction coefficients gL and gR in Formula (21) described above obtained, the composite vector CV and the superimposed vector CR match if the positional relationship matches between the image IL(x,δ) and the image IL'(x) and the positional relationship matches between the image IL(x,δ,s) and the image IR'(x).

The motion amount δ and the phase difference s can be searched for by detecting the position at which the vector CV and the vector CR match while correcting the magnitudes of the vectors VL and VR in Formula (21) described above. Thus, the motion amount δ and the phase difference s can be accurately obtained. In other words, the vectors VL and VR, which are components of the vector CV, are normalized to match the component ratio between the vectors RL and RR, and then the vector CV and the vector CR are compared with each other. Thus, the matching evaluation can be properly performed with the matching level between the vector CR and the vector CV increased.

Figure 19:
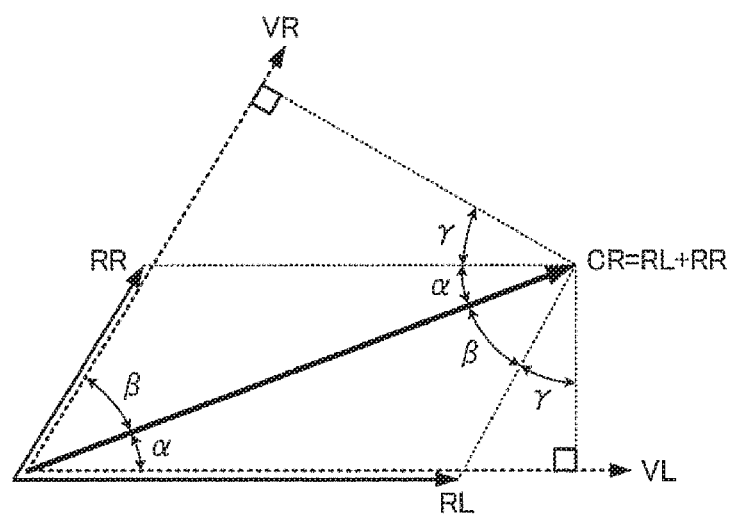
FIG. 19 illustrates the third phase difference detection method.
Figure 20:
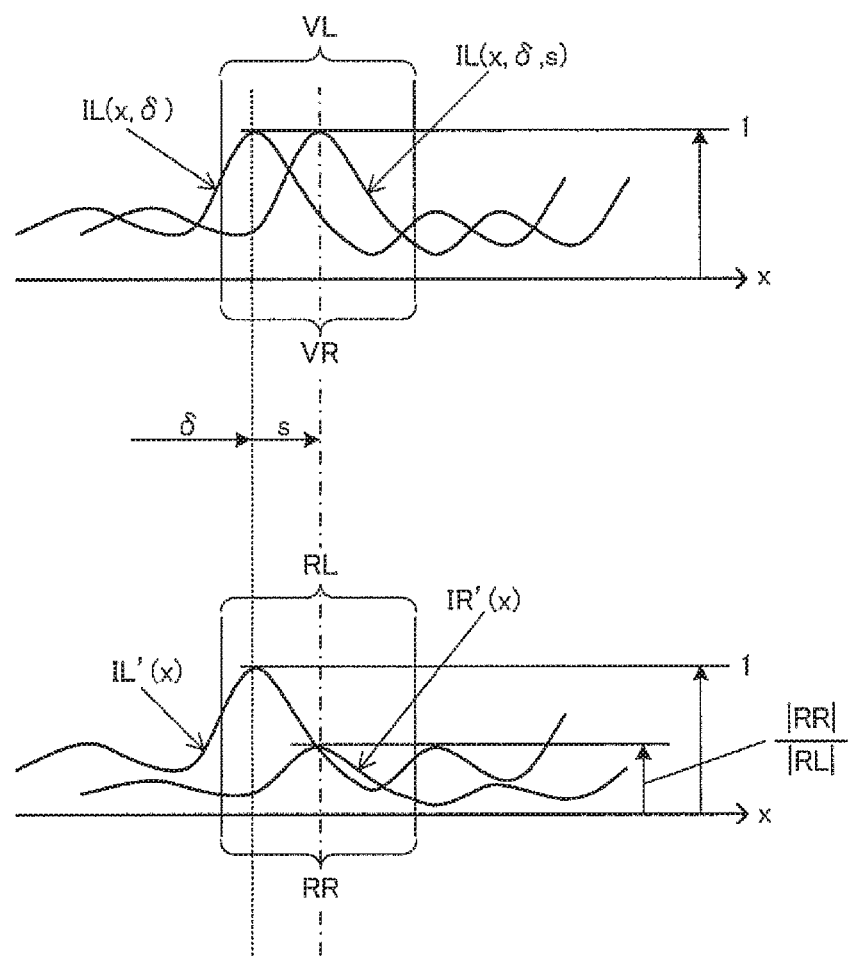
FIG. 20 illustrates the third phase difference detection method.

First of all, the magnitudes of the vectors RL and RR, which are components of the detected vector CR corresponding to the superimposed image ILR'(x), are obtained. The image IL(x,δ) and the image IL'(x) as well as the image IL(x,δ,s) and the image IR'(x) are regarded as being in similar relationship within a limited calculation range w. Thus, directions of the vector VL and the vector RL as well as directions of the vector VR and the vector RR can be assumed to match if the positions of the vectors match even when the vectors have difference magnitudes. FIG. 19 is a schematic view illustrating relationship among vectors.

An angle between the vector CR and the vector RL, that is, an angle between the vector CR and the vector VL is defined as α. An angle between the vector CR and the vector RR, that is, an angle between the vector CR and the vector VR is defined as β. The relationship in the following Formula (22) can be obtained with the angles α and β.

$$\left. \begin{aligned} VL \cdot CR &= |VL||CR|\cos\alpha \\ VR \cdot CR &= |VR||CR|\cos\beta \\ \gamma &= \pi/2 - (\cos\alpha + \cos\beta) \end{aligned} \right\} \quad (22)$$

Angles α, β, and γ are obtained with Formula (22) described above and are substituted into the following Formula (23). Thus, magnitudes |RL| and |RR| of the vectors RL and RR can be obtained.

$$\left. \begin{aligned} |RL| &= |CR|\cos\alpha - |CR|\sin\beta \cdot \tan\gamma \\ |RR| &= |CR|\cos\beta - |CR|\sin\alpha \cdot \tan\gamma \end{aligned} \right\} \quad (23)$$

The following Formula (24) is obtained based on Formula (21) described above.

$$|RL| = gL \cdot |VL|, |RR| = gR \cdot |VR| \quad (24)$$

The following Formula (25) is obtained based on Formula (24) described above.

$$gL = \frac{|RL|}{|VL|}, gR = \frac{|RR|}{|VR|} \quad (25)$$

The correction coefficient gL and gR can be obtained by substituting |RL| and |RR|, obtained with Formula (23) described above, in to Formula (25) described above.

A vector NCV is newly obtained by combining the vector VL and VR after having the component amounts (magnitudes) corrected by using the correction coefficients gR and gL thus obtained. The following Formula (26) is obtained based on Formula (21) described above.

$$NCV=gL \cdot VL+gR \cdot VR=RL+RR \quad (26)$$

All things considered, when the vector CR and the vector NCV match, the positional relationship substantially match between the vector VL and the vector RL and between the vector VR and the vector RR.

Note that the directions of the vector RL and the vector RR are the same if the superimposed image ILR'(x) involves no phase difference s' as in the following Formula (27). In such a case the coefficients gL and gR cannot be identified from the calculation method described above.

$$\alpha=0 \text{ and } \beta=0 \quad (27)$$

Still, in such a case, the direction of the search vector VL matches the direction of the vector RL, and the direction of the search vector VR matches the vector RR. Note that the directions might be closest as much as possible instead of matching due to a degrading factor such as noise.

Thus, a position at which the angle $\alpha$ and the angle $\beta$ are both the smallest as much as possible is identified and evaluated as the position where the motion amount $\delta'$ matches. The angle $\alpha$ and the angle $\beta$ are both determined to be the smallest as much as possible with a smallest value of $(\alpha+\beta)$ (a value close to 0), where $\alpha>0$ and $\beta>0$. For example, a matching evaluation function E as in the following Formula (28) is used.

$$E=(\alpha+\beta) \cdot |NCV-CR| \quad (28)$$

The evaluation function is not limited to this, and may be $E=(\alpha+\beta) \cdot (1-NCC[NCV,CR])$ for example. NCC[NCV,CR] is a value indicating correlation between vectors NCV and CR, obtained with ZNCC.

The correction coefficients gL and gR of appropriate values are obtained with Formula (21) to (25) described above only when the vector CV and the vector CR match. In other words, only the correction coefficients gL and gR of inappropriate values (invalid values) are obtained during the search for the phase difference s and the motion amount $\delta$, if the vector CV and the vector CR do not match. Thus, a case of applying the correction coefficients gL and gR obtained with Formulae (21) to (25) described above without successful matching, that is, with the directions of the vectors CV and CR not matching is more likely to result in a failure to match the vectors CV and CR than in a case of not applying the coefficients. This feature is favorable in terms of matching position detection.

The embodiments and the modifications thereof according to the present invention are described. However, the present invention is not limited the embodiments and the modifications only, and the present invention can be implemented with the elements modified without departing from the gist of the invention. The plurality of elements disclosed in the embodiments and the modifications may be combined as appropriate to implement the invention in various ways. For example, some of all the elements described in the embodiments and the modifications may be deleted. Furthermore, elements in different embodiments and modifications may be combined as appropriate. Thus, various modification and application can be made without departing from the gist of the present invention. Any term cited with a different term having a broader meaning or the same meaning at least once in the specification and the drawings can be replaced by the different term in any place in the specification and the drawings.

What is claimed is:

1. An imaging device comprising: an image sensor;
an optical system forming an image of an object on the image sensor; and
a processor,
the optical system switching between a first state of capturing an image of the object with a single pupil and a second state of capturing an image of the object with two pupils,
the processor being configured to implement generating a simulative phase difference image from a first captured image captured with the image sensor in the first state, and executing matching processing of comparing the simulative phase difference image with a second capture image captured with the image sensor in the second state to detect a phase difference between an image formed with one of the two pupils and an image formed with another one of the two pupils.

2. The processor as defined in claim 1,
the processor being configured to implement
generating a first simulative pupil image corresponding to the image formed with the one of the pupils and a second simulative pupil image corresponding to the image formed with the other one of the pupils, from the first captured image,
generating the simulative phase difference image through processing of adding together the first simulative pupil image and the second simulative pupil image shifted from each other by a shifting amount corresponding to the phase difference, and
detecting the phase difference through the matching processing while changing the shifting amount.

3. The imaging device as defined in claim 1,
the two pupils of the optical system have difference sizes.

4. The imaging device as defined in claim 3,
the processor being configured to implement
generating the first simulative pupil image corresponding to the image formed with the one of the pupils and the second simulative pupil image corresponding to the image formed with the other one of the pupils, with gain adjustment, based on the different sizes of the two pupils, executed on the first captured image,
generating the simulative phase difference image through processing of adding together the first simulative pupil image and the second simulative pupil image shifted from each other by a shifting amount corresponding to the phase difference, and
detecting the phase difference through the matching processing while changing the shifting amount.

5. The imaging device as defined in claim 1,
the processor being configured to implement further detecting a motion amount due to an object moving between the first captured image and the second captured image, based on the first captured image and the second captured image.

6. The imaging device as defined in claim 5,
the processor being configured to implement
generating a first simulative pupil image corresponding to the image formed with the one of the pupils and a second simulative pupil image corresponding to the image formed with the other one of the pupils, from the first captured image,
generating the simulative phase difference image through processing of adding together the first simulative pupil image and the second simulative pupil image shifted from each other by a first shifting amount corresponding to the phase difference and by a second shifting amount corresponding to the motion amount, and detecting the phase difference and the motion amount through the matching processing while changing the first shifting amount and the second shifting amount independently from each other.

7. The imaging device as defined in claim 1, the optical system is set to be in the first state in an n-th frame and is set to be in the second state in n+1-th to n+j-th frames after the n-th frame, n being an integer, j being an integer that is equal to or larger than two, the processor being configured to implement detecting the phase difference, based on the first captured image captured in the n-th frame and the second captured image captured in an n+i-th frame, in the n+1-th to the n+j-th frames, for j times, and executing processing of averaging the j phase differences, i being an integer that is equal to larger than one and is equal to or smaller than j.

8. The imaging device as defined in claim 1, the processor being configured to implement outputting an observation image based on the first captured image.

9. The imaging device as defined in claim 1, the optical system including:

a fixed mask including a first opening and a second opening; and a movable mask that is movable relative to the fixed mask, in the first state, the movable mask not closing the first opening and closing the second opening, and the optical system forming the image of the object using the first opening as the single pupil, in the second state, the movable mask not closing the first opening or the second opening, and the optical system forming the image of the object using the first opening and the second opening as the two pupils.

10. The imaging device as defined in claim 9, the second opening being smaller than the first opening in the fixed mask.

11. The imaging device as defined in claim 1, the optical system including:

a fixed mask including an opening; and a movable mask that is movable relative to the fixed mask, in the first state, the movable mask not splitting the opening, and the optical system forming the image of the object using the opening not split as the single pupil, in the second state, the movable mask splitting the opening into a first split opening and a second split opening smaller than the first split opening, and the optical system forming the image of the object using the first split opening and the second split opening as the two pupils.

12. The imaging device as defined in claim 1, the processor being configured to implement performing control to switch between a first mode of setting the optical system to be in the first state and a second mode of setting the optical system to be in the second state.

13. The imaging device as defined in claim 12, the processor being configured to implement detecting at least one of the optical system set to be in the first state under the first mode and the optical system set to be in the second state under the second mode, based on an image captured under the first mode and an image captured under the second mode.

14. An endoscope apparatus comprising the imaging device as defined in claim 1.

15. An imaging method comprising:

switching a state of an optical system between a first state in which the optical system forms an image of an object on an image sensor with one pupil and a second state in which the optical system forms the image of the object on the image sensor with two pupils, generating a simulative phase difference image from a first captured image captured with the image sensor in the first state, executing matching processing to compare the simulative phase difference image with a second captured image captured with the image sensor in the second state, and detecting a phase difference between an image formed with one of the two pupils and an image formed with another one of the two pupils.

* * * * *